US012280146B2

(12) United States Patent
Foguet et al.

(10) Patent No.: US 12,280,146 B2
(45) Date of Patent: Apr. 22, 2025

(54) NANOEMULSION WITHOUT PROPYLENE GLYCOL

(71) Applicant: Biofrontera Bioscience GmbH, Leverkusen (DE)

(72) Inventors: Montserrat Foguet, Leverkusen (DE); Lars Möllmann, Leverkusen (DE)

(73) Assignee: Biofrontera Bioscience GmbH, Leverkusen (DE)

( * ) Notice: Subject to any disclaimer, the term of this patent is extended or adjusted under 35 U.S.C. 154(b) by 0 days.

(21) Appl. No.: 18/533,497

(22) Filed: Dec. 8, 2023

(65) Prior Publication Data

US 2024/0335380 A1    Oct. 10, 2024

(30) Foreign Application Priority Data

Apr. 6, 2023    (WO) ............... PCT/EP2023/059291

(51) Int. Cl.
| | | |
|---|---|---|
| A61K 9/107 | (2006.01) | |
| A61K 9/127 | (2006.01) | |
| A61K 41/00 | (2020.01) | |
| A61K 47/10 | (2017.01) | |
| A61K 47/12 | (2006.01) | |
| A61K 47/14 | (2017.01) | |
| A61K 47/24 | (2006.01) | |
| A61K 47/26 | (2006.01) | |
| A61K 47/36 | (2006.01) | |

(52) U.S. Cl.
CPC ............ *A61K 9/1075* (2013.01); *A61K 9/127* (2013.01); *A61K 41/0061* (2013.01); *A61K 47/10* (2013.01); *A61K 47/12* (2013.01); *A61K 47/14* (2013.01); *A61K 47/24* (2013.01); *A61K 47/26* (2013.01); *A61K 47/36* (2013.01)

(58) Field of Classification Search
None
See application file for complete search history.

(56) References Cited

U.S. PATENT DOCUMENTS

| | | | |
|---|---|---|---|
| 5,152,923 A * | 10/1992 | Weder ............... | A61Q 19/00 424/455 |
| 5,891,490 A | 4/1999 | Merabet | |
| 6,165,500 A | 12/2000 | Cevc | |
| 6,245,349 B1 | 6/2001 | Yiv et al. | |
| 6,274,150 B1 | 8/2001 | Simonnet et al. | |
| 6,375,960 B1 | 4/2002 | Simonnet et al. | |
| 6,413,527 B1 | 7/2002 | Simonnet et al. | |
| 6,500,862 B1 | 12/2002 | Zanello | |
| 6,559,183 B1 * | 5/2003 | Schmid ............... | A61P 17/06 514/561 |
| 6,602,511 B2 | 8/2003 | Von Corswant | |
| 6,897,238 B2 | 5/2005 | Chen et al. | |
| 7,314,624 B2 | 1/2008 | Baker et al. | |
| 11,540,981 B2 | 1/2023 | Roca et al. | |
| 2002/0155084 A1 | 10/2002 | Roessler et al. | |
| 2003/0148927 A1 | 8/2003 | Patt et al. | |
| 2003/0167033 A1 | 9/2003 | Chen et al. | |
| 2003/0190347 A1 | 10/2003 | Supersaxo et al. | |
| 2005/0158389 A1 | 7/2005 | Domb | |
| 2005/0208083 A1 | 9/2005 | Annis | |
| 2006/0078525 A1 | 4/2006 | Tomokuni | |
| 2006/0140984 A1 | 6/2006 | Tamarkin et al. | |
| 2009/0110703 A1 | 4/2009 | Tolla et al. | |
| 2009/0324727 A1 * | 12/2009 | Foguet Roca ......... | A61K 9/107 514/561 |
| 2011/0060042 A1 | 3/2011 | Ito | |
| 2023/0201087 A1 | 6/2023 | Roca et al. | |

FOREIGN PATENT DOCUMENTS

| | | |
|---|---|---|
| EP | 0620271 A1 | 10/1994 |
| EP | 0704209 A1 | 4/1996 |
| EP | 1473367 A1 | 11/2004 |
| EP | 1655021 A1 | 5/2006 |
| JP | 2002-302414 A | 10/2002 |
| JP | 2006-273821 A | 10/2006 |
| WO | WO 1996/041647 A1 | 12/1996 |
| WO | WO 1997/041855 A1 | 11/1997 |
| WO | WO 1998/021307 A1 | 5/1998 |
| WO | WO 2002/066589 A2 | 8/2002 |
| WO | WO 2005/027872 A2 | 3/2005 |
| WO | WO 2005/110370 A1 | 11/2005 |

OTHER PUBLICATIONS

U.S. Appl. No. 12/520,759 2009/0324727 U.S. Pat. No. 11,540,981, filed Dec. 22, 2006 Dec. 21, 2007 Jan. 3, 2023, Montserrat Foguet Roca, Nanoemulsion Formulation with Improved Stability and Cell Penetration.
U.S. Appl. No. 18/071,733 2023/0201087, filed Nov. 30, 2022 Jun. 29, 2023, Montserrat Foguet Roca, Nanoemulsion.
U.S. Appl. No. 18/533,521, filed Dec. 8, 2023, Montserrat Fouget, Pressurized Nanoemulsion.
Aboofazeli et al., "Particle Size Analysis of Concentrated Phospholipid Microemulsions: I. Total Intensity Light Scattering", AAPS PharmSci, 2000, 2(2): 1-13.
Alam et al., "Design and Characterization of Nanostructured Topical Gel of Betamethasone Dipropionate for Psoriasis," Journal of Applied Pharmaceutical Science, 2012, 2(10): 148-158.
Bagwe et al., "Improved Drug Delivery Using Microemulsions: Rationale, Recent Progress, and New Horizons", Critical Reviews in Therapeutic Drug Carrier Systems, 2001, 18(1): 77-140.

(Continued)

*Primary Examiner* — Celeste A Roney
(74) *Attorney, Agent, or Firm* — Lathrop GPM LLP; James H. Velema; Laura A. Labeots

(57) ABSTRACT

The present invention relates to oil in water nanoemulsions which are essentially free of propylene glycol. The nanovesicle formulations are particularly stable in regard to shelf life at different storage temperatures.

17 Claims, 6 Drawing Sheets

(56) References Cited

OTHER PUBLICATIONS

Figure 1:
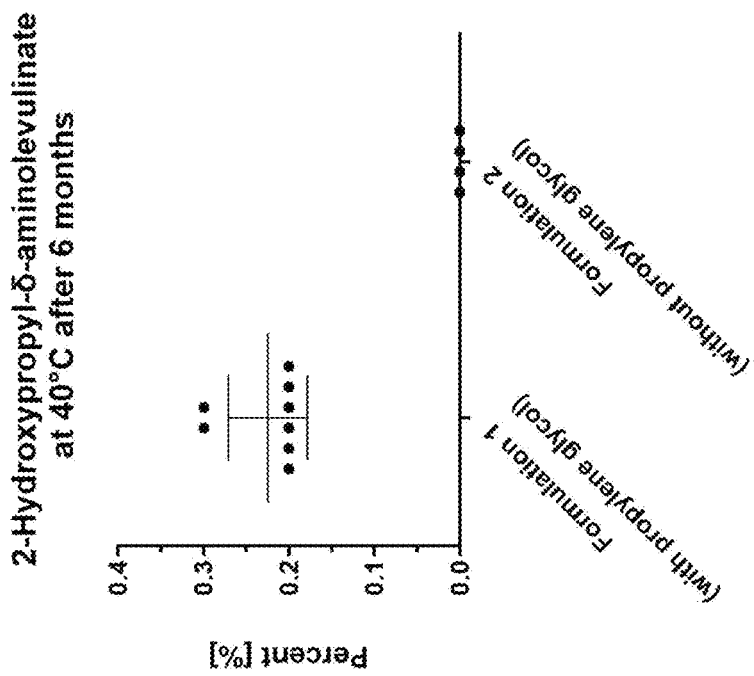
Figure 1:
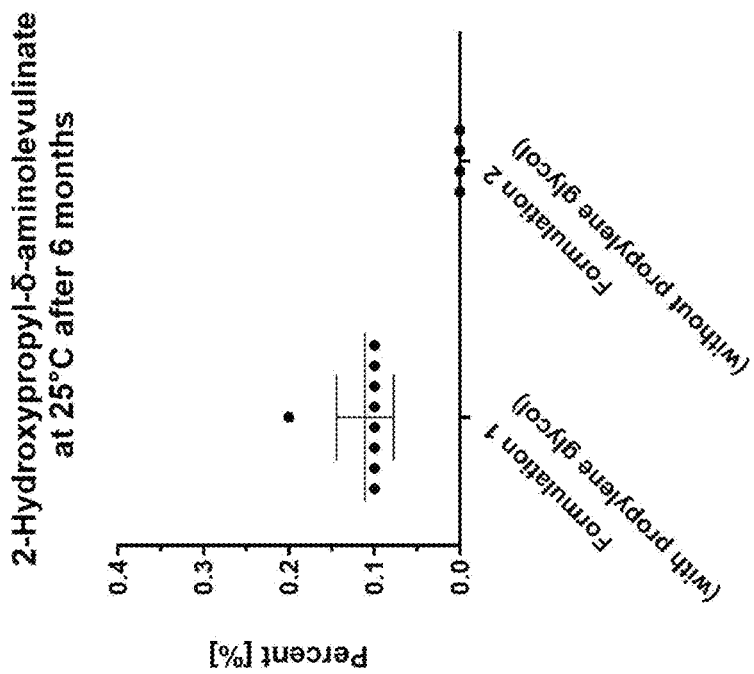
Figure 1:
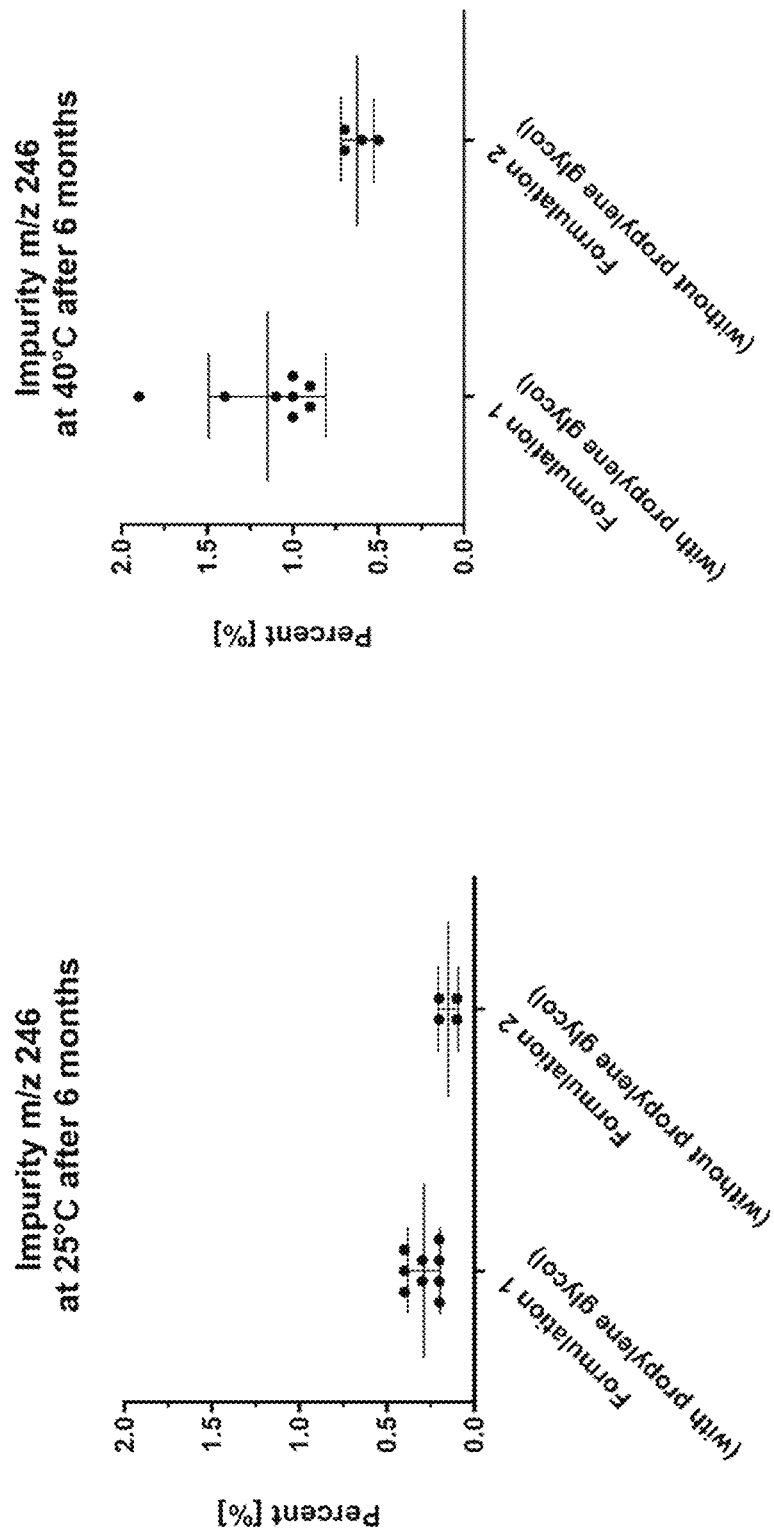

Binks et al., "Phase Behaviour of microemulsions stabilised by double chain cationic surfactants and alcohol co-surfactants", Colloids and Surfaces A: Physicochem. Eng. Aspects, Jan. 23, 2003, 212(2-3): 135-145.
Danielsson et al., "The Definition of Microemulsion", Colloids and Surfaces, Dec. 1981, 3(4): 391-392.
Fendler et al., "Liposomes as Drug Carriers", Life Sciences, Apr. 1, 1977, 20(7):1109-1120.
Fritsch et al., "Fluorescence Diagnosis and Photodynamic Therapy of Skin Diseases", Atlas and Handbook, 2003, pp. 23-31.
International Food Information Service, "Dictionary of Food Science and Technology", 2nd ed. 2009, p. 250.
International Search Report and Written Opinion for PCT International Patent Application No. PCT/EP2007/011404, dated May 9, 2008.
Kang et al., "Preparation and Characterization of Nano-Liposomes Using Phosphatidylcholine", International Journal of Industrial and Engineering Chemistry, Nov. 2005, 11(6): 847-851.
Kosar et al., "Exogenously-applied 5-aminolevulinic acid modulates some key physiological characteristics and antioxidative defense system in spring wheat (*Triticum aestivum* L.) seedlings under water stress," Journal of Botany, 2015, 96: 71-77.
Moreno, "Lecithin-Based Oil-in-Water Microemulsions for Parenteral Use: Pseudoternary Phase Diagrams, Characterization and Toxicity Studies", Wiley-Liss Journal of Pharmaceutical Science, 2003, 92(7): 1428-1437.
O'Neil et al., "The Merck Index: An Encyclopedia of Chemicals, Drugs, and Biologicals," Merck & Co., Inc.; entries for "aminolevulinic acid," "Lecithins," and "Polysorbates," 2006, pp. 1-8 (as provided).
Sarker, "Engineering of Nanoemulsions for Drug Delivery", Current Drug Delivery, Oct. 2005, 2(4): 297-310.
Sinko et al., "Martin's Physical Pharmacy and Pharmaceutical Sciences", Physical Chemical and Biopharmaceutical Principles in the Pharmaceutical Sciences, 15th ed., 2009, Chapter 18, "Coarse Dispersions" pp. 499-530.
Sonneville-Aubrun et al., "Nanoemulsions: a new vehicle for skincare products", Advanced Colloid and Interface Science, May 20, 2004, 108-109: 145-149.
Suppasansatorn et al., "Microemulsions as topical delivery vehicles for the anti-melanoma prodrug, temozolomide hexyl ester (TMZA-HE)", Journal of Pharmacy and Pharmacology, Jun. 2007, vol. 59, pp. 787-794.
Tadros et al., "Formation and stability of nano-emulsions", Advances in Colloid and Interface Science, May 20, 2004, vol. 108-109, pp. 303-318.
Weiss et al., "Nanostructured Encapsulation Systems: Food Antimicrobials", Global Issues in Food Science and Technology, 2009, Chapter 24, pp. 425-479.
Yuan et al., "Investigation of microemulsion system for transdermal delivery of meloxicam", International Journal of Pharmaceutics, Sep. 14, 2006, 321(1-2):117-123.
Acharaya et al., "Physicochemical Investigations of Microemulsification of Coconut Oil and Water Using Polyoxyethylene 2-Cetyl Ether (Brij 52) and Isopropanol or Ethanol", Journal of Colloid and Interface Science, 2002, 245: 163-170.
Changez et al., "Effect of the composition of lecithin/n-propanol/isopropyl myristate/water microemulsions on barrier properties of mice skin for transdermal permeation of tetracaine hydrochloride: In vitro", Colloids and Surfaces B: Biointerfaces, 2006, 50: 18-25.
De Spiegeleer et al., "The Importance of the Cosolvent Propylene Glycol on the Antimicrobial Preservative Efficacy of a Pharmaceutical Formulation by DOE—Ruggedness Testing", Informa Healthcare; Pharmaceutical Development and Technology, 2006, 11: 275-284.

* cited by examiner

NANOEMULSION WITHOUT PROPYLENE GLYCOL

RELATED APPLICATIONS

This application claims priority to International Patent Application No. PCT/EP2023/059291, filed Apr. 6, 2023, the entire disclosure of which is hereby incorporated herein by reference.

DESCRIPTION

The present invention relates to a composition for topical use comprising an oil in water nanoemulsion and an active ingredient, wherein the composition is essentially free of propylene glycol. The formulation shows less impurities and side products of the active ingredient over time and therefore ensures a higher quality standard and an improved shelf-life.

BACKGROUND OF THE INVENTION

Dispersions are colloidal systems, which include micelles, liposomes, virosomes, emulsions and micro-, nanoemulsions, suspensions and polymer solutions. Emulsions or micro emulsions can be oil in water, water in oil or middle phased dispersions, often dispersed with surfactants as emulsifiers. Nanoemulsions are a subgroup of the emulsions that contain very fine oil in water dispersions. Nanoemulsions are highly homogeneous, transparent, and slightly opalescent dispersions (or emulsions) of oil and water. The dispersed droplets (liquid) or vesicles in such emulsions are composed of a lipid core surrounded by at least one surfactant or emulsifier monolayer. Nanoemulsions are characterized by a mean particle or vesicle size of less than 200 nm, often less than 100 nm and a narrow monodisperse particle or vesicle size distribution. Nanoemulsions are thermodynamically more stable than conventional emulsions, making them a favorable vehicle for pharmaceutical compositions, which have to maintain stability for long periods of time. Nanoemulsions can be in a metastable state and the structure depends often of the manufacturing process, making them a fragile system and complicated to formulate to a pharmaceutical composition with a long shelf-life under different storage conditions. If destabilized they can become heterogeneous, milky and/or exhibit phase separation. However, they can provide useful applications in skin care in that they may exhibit good textural and sensual properties due to the very fine droplet or globule size.

Nanoemulsions are generally manufactured by mechanical fragmentation of an oily phase in an aqueous phase in the presence of a surfactant. The very small size of the oily globules is often obtained by virtue of at least one pass through a high-pressure homogenizer or a sonicator.

Formulations comprising nanoemulsions as vehicles for the delivery of active ingredients often contain adjuvants, such as organic molecules or solvents, e.g., propylene glycol. Propylene glycol is known to have advantageous properties, such as penetration enhancing or preservative effects (Carrer et al., Effect of propylene glycol on the skin penetration of drugs. Arch Dermatol Res 312, 337-352 (2020), https://doi.org/10.1007/s00403-019-02017-5, McGowan M A et al., Propylene Glycol in Contact Dermatitis: A Systematic Review. Dermatitis, 2018; 29 (1): 6-12, doi: 10.1097/DER.0000000000000307). Additionally, it is known to be an excellent solvent for other adjuvants or other ingredients and to be an excellent emulsifier. However, cases have been reported in which patients with atopic dermatitis show allergic reactions to propylene glycol and it is known to be irritating to the eyes. Furthermore, it is a diol and may undergo unwanted side reactions, due to its nucleophilic nature. Such reactions are known for example with sorbitol or glycerol in the presence of cetirizine, which is well known as an anti-allergic compound.

Propylene glycol is commonly used as a solvent of hydrophilic compounds. For example, parabens are only slightly soluble in water. In the preparation of an aqueous pharmaceutical formulation or a formulation comprising an aqueous component, parabens must be solved in a solvent, such as propylene glycol, suitable to introduce the parabens in the aqueous phase.

5-aminolevulinic acid (also termed herein "ALA" or "5-ALA") is a small biogenic amino acid with a molecular weight (as HCl salt) of 167.59 g/mol and is very hydrophilic, i.e. readily soluble in water with octanol-water partition coefficient (log P) of around -3. ALA is used in Photodynamic Therapy (PDT) as a prodrug to drive the synthesis of protoporphyrin IX in diseased tissue, which is subsequently illuminated with light of appropriate wavelengths to induce the photodynamic effect.

Known formulations of ALA for topical use on the skin, are instable in aqueous solutions (see Reinhold, Future Oncology, 2017 November; 13 (27): 2413-2428, doi: 10.2217/fon-2017-0247). So far, the nanoemulsion put to use with ALA contained 10% active ingredient and was formulated as a gel. The previous gel formulation showed stability up to 36 months at refrigerated temperatures (2-8° C.) but was susceptible to higher temperatures (standard room temperature and above). Exposure to higher temperatures was tolerated in the range of few weeks without risking pharmaceutical quality for human use.

SUMMARY OF THE INVENTION

A first aspect of the invention relates to a formulation comprising (a) a nanoemulsion comprising: (i) at least one aqueous component; (ii) a carrier component comprising: (1) at least one lipophilic component, (2) at least one surfactant, and (3) at least one alcohol; and (b) an active agent comprising a carboxylic acid group, or a derivative, or salt of a carboxylic acid group, wherein the formulation comprises less than 1% w/w of propylene glycol or no propylene glycol.

Another aspect of the invention relates to the formulation of the first aspect for use in a method of treatment and/or prevention of a dermatological disease or condition.

Another aspect of the invention relates to a method for the preparation of the formulation as described herein, comprising the following steps: (a) mixing the at least one lipophilic component, the at least one surfactant, and the at least one alcohol having at least three carbon atoms, and (b) contacting the mixture obtained in step (a) with an aqueous component, under conditions allowing formation of a nanoemulsion, wherein the active agent is added under conditions allowing interactions of the active agent with the surface of the nanovesicles when dissolved in the aqueous phase.

DETAILED DESCRIPTION

Before the present invention is described in detail below, it is to be understood that this invention is not limited to the particular methodology, protocols and reagents described herein as these may vary. It is also to be understood that the terminology used herein is for the purpose of describing particular embodiments only, and is not intended to limit the scope of the present invention, which will be limited only by the appended claims. Unless defined otherwise, all technical and scientific terms used herein have the same meanings as commonly understood by one of ordinary skill in the art.

Preferably, the terms used herein are defined as described in "A multilingual glossary of biotechnological terms: (IUPAC Recommendations)", Leuenberger, H. G. W, Nagel, B. and Kölbl, H. eds. (1995), Helvetica Chimica Acta, CH-4010 Basel, Switzerland).

Several documents are cited throughout the text of this specification. Each of the documents cited herein (including all patents, patent applications, scientific publications, manufacturers' specifications, instructions etc.), whether supra or infra, is hereby incorporated by reference in its entirety.

In the following, the elements of the present invention will be described. These elements are listed with specific embodiments, however, it should be understood that they may be combined in any manner and in any number to create additional embodiments. The variously described examples and preferred embodiments should not be construed to limit the present invention to only the explicitly described embodiments. This description should be understood to support and encompass embodiments, which combine the explicitly described embodiments with any number of the disclosed and/or preferred elements. Furthermore, any permutations and combinations of all described elements in this application should be considered disclosed by the description of the present application unless the context indicates otherwise.

Throughout this specification and the claims which follow, unless the context requires otherwise, the word "comprise", and variations such as "comprises" and "comprising", are to be understood to imply the inclusion of a stated integer or step or group of integers or steps but not the exclusion of any other integer or step or group of integer or step. As used in this specification and the appended claims, the singular forms "a", "an", and "the" include plural referents, unless the content clearly dictates otherwise.

Formulating a topical pharmaceutical gel composition is a highly complex process, which needs to take account of different aspects, such as pH, solubility, polymorphism, applicability, and overall stability of the pharmaceutical composition. Additionally, one must consider the benefits and constraints of the active pharmaceutical ingredient (API), excipients, the interaction of all components and the manufacturing process. In oil in water nanoemulsion formulations, there are two different phases, which may need to be stabilized and compliant with patients: one is the hydrophobic carrier component, which is usually the carrier and needs to stabilize and release the API and the other one the aqueous component. All these aspects lead to complex formulations with a large number of ingredients. However, the more ingredients a composition has, the more problems/pitfalls may arise during formulation, such as undesired side reactions/interactions of ingredients or higher impurity profiles. Additionally, patients may have allergic reactions or skin irritations to various components after application on the skin. Therefore, a pharmaceutical composition should only have the necessary ingredients and omit as many adjuvants and/or excipients as possible. One very popular class of excipients in cosmetics, pharmaceutical or food products are polyols, in particular propylene glycol. It may be used as a solvent, humectant, preservative agent or emulsion stabilizer. One rather attractive property in topical pharmaceuticals is its ability to enhance penetration of active ingredients.

The prior art fails to teach a pharmaceutical composition comprising a nanoemulsion composition containing an active agent comprising a carboxylic acid group or a derivative, or pharmaceutically acceptable salt of a carboxylic acid group, being free of propylene glycol.

In the context of the present specification, the term "propylene glycol" refers to propane-1,2-diol (also known as 1,2-propanediol, α-propylene glycol, 1,2-dihydroxypropane, methyl ethyl glycol or methylethylene glycol).

As described above, nanoemulsions tend to coalesce under certain circumstances, such as exposure to extreme temperature differences, leading to bigger droplet sizes and harm the nanoemulsion quality.

These aspects make it clear that design and formulation of a composition with a high penetration and improved impurity profile is highly desirable.

The examples of the present invention demonstrate that the omission of propylene glycol in a pharmaceutical formulation comprising an active agent, in particular an hydrophilic active agent and/or an active agent comprising a carboxylic acid group or a derivative, or pharmaceutically acceptable salt of a carboxylic acid shows a better impurity profile without restricting the penetration properties of the topical pharmaceutical composition compared to a pharmaceutical formulation comprising propylene glycol. Surprisingly, the penetration of the vehicles is improved by the omission of propylene glycol, which is a non-obvious discovery for a person skilled in the art.

The terms "active agent" and "active ingredient" are used interchangeably herein. As used herein, "active agent", includes an active pharmaceutical agent (herein also termed "pharmaceutical active agent" or "active pharmaceutical ingredient", "API") and an active cosmetic agent (herein also termed "cosmetic active agent"). As used herein, an active pharmaceutical agent is defined as the chemical, biological, mineral or any other entity or component responsible for the therapeutic (pharmacological, physiological, physical, etc.) effects in a product. As used herein, an active cosmetic agent is defined as the chemical, biological, mineral or any other entity or component responsible for the cosmetic effects in a product. The active agent may be a plant extract. The active agent may be present as a pharmaceutically acceptable salt. The active agent may be present as a cosmetically acceptable salt.

In the following specification, unless specifically mentioned otherwise, the term "active agent comprising a carboxylic acid group" also refers to active agents comprising a derivative of a carboxylic acid group, or a salt of a carboxylic acid group.

Preferably, the active agent comprising a carboxylic acid group is a hydrophilic active agent. It is preferred that the hydrophilic active agent has a log P value equal to or lower than 1, lower than 0.5, lower than 0.4, lower than 0.3, lower than 0.2, lower than 0.1 or a negative lg P value, wherein P is the octanol-water partition-coefficient.

In the context of the present specification, the term "derivative of a carboxylic acid group" refers to a carboxylic acid group that has formed a chemical compound by reacting with another chemical moiety, in particular a carboxylic acid group that has formed an ester by reacting with a hydroxy group.

Without wishing to be bound by theory, active agents comprising a carboxylic acid group may undergo nucleophilic reactions to form undesired products, such as esters, with propylene glycol. In instances where the active agent comprises a derivative of carboxylic acid group in the form of an ester, the active agent may still undergo nucleophilic reactions to form undesired products, such as esters, with propylene glycol, e.g. via transesterification. Omission of propylene glycol may thus lead to less undesired side products.

In addition to an extinction of the expected esters formed by 5-ALA and propylene glycol, the examples show that in a 5-ALA gel formulation of the invention, being free of propylene glycol, a previously detected impurity with m/z of 246 was surprisingly greatly reduced. This reduction is a meaningful improvement in view of prior art formulations: Firstly, this impurity poses the highest probability for "out-of-specification" results during stability testing. Secondly, the amount of this impurity increases at higher temperatures and after longer storage. A reduction of this impurity, as observed in the formulation of the invention, being free of propylene glycol, improves stability under stressed conditions and allows for longer storage. Additionally, the unknown impurities may be harmful for patients, since it is impossible to predict their metabolism and long-term influence on the human body.

Furthermore, functional in vitro tests described in the Examples revealed that omission of propylene glycol does not impair the drug release and skin penetration qualities of the formulation at any rate. Improved penetration results of ALA were achieved with the formulation of the invention without propylene glycol compared to comparative formulation with propylene glycol. The formulation without propylene glycol has non-inferior penetration properties compared to the formulation containing propylene glycol. This finding is surprising, as propylene glycol is a well-known and highly effective penetration enhancer used in topical pharmaceutical formulations.

In an in-vitro release assay, the formulation of the invention, being free of propylene glycol, released more 5-ALA than the comparative formulation comprising propylene glycol. This finding is surprising since the addition of polyols, in particular glycerol or propylene glycol, which does not evaporate upon application, is expected to improve adhesion and thus improves drug release.

The formulations of the invention comprise two phases:
(I) an aqueous phase or aqueous component,
(II) a lipid carrier phase.

A first aspect of the invention relates to a formulation comprising
(a) a nanoemulsion comprising:
  (i) at least one aqueous component;
  (ii) a carrier component comprising:
    (1) at least one lipophilic component,
    (2) at least one surfactant, and
    (3) at least one alcohol; and
(b) an active agent comprising a carboxylic acid group, or a derivative, or salt of a carboxylic acid group,
wherein the formulation comprises less than 1% w/w of propylene glycol or no propylene glycol.

In preferred embodiments, the formulation is a pharmaceutical formulation.

In some embodiments, the formulation is a lotion, a spray, a foam, an emulsion, a nanoemulsion, a gel or a cream. In some embodiments, the formulation is a lotion. In the context of the present specification, a lotion is a low-viscosity topical preparation intended for application to the skin. A lotion has a lower viscosity than a cream or a gel due to its higher water content. In some embodiments, the lotion has a viscosity of ≤8 Pas (pascal-second), ≤6 Pa s, ≤5 Pas, ≤4 Pa s, ≤3 Pa s, ≤1.0 Pa s, or ≤0.5 Pa s.

The skilled person is aware of suitable methods for determining the viscosity. Preferably, the viscosity is determined as described in the examples section.

In preferred embodiments, the formulation is for topical use.

In preferred embodiments of the formulations described in the present invention, the aqueous component comprises an aqueous phase or forms an aqueous phase. Preferably, the active agent is dissolved in the aqueous phase.

In preferred embodiments of the formulations described in the present invention, the carrier component comprises or consists of nanovesicles. Preferably, the active agent is capable to interact with the surface of the nanovesicles.

The active agent may be present as a salt. Examples in which the active agent is present as a salt are e.g. 5-aminolevulinic acid HCl, and 5-aminolevulinic acid phosphate.

In even more preferred embodiments of the formulations described in the present invention, the active agent is dissolved in the aqueous phase and is capable to interact with the surface of the nanovesicles. The active agent preferably comprises a carboxylic acid group, a derivative of a carboxylic acid group, or pharmaceutically acceptable salt of a carboxylic acid group.

Examples in which the active agent comprises a derivative of a carboxylic acid group are e.g. esters of 5-aminolevulinic acid such as methyl δ-aminolevulinate (MAL), and hexyl O-aminolevulinate (HAL).

Examples in which the active agent comprises a pharmaceutically acceptable salt of a derivative of a carboxylic acid group are e.g. methyl δ-aminolevulinate hydrochloride, hexyl O-aminolevulinate hydrochloride.

In all embodiments described herein, the salt of a carboxylic acid group is preferably a pharmaceutically acceptable salt of a carboxylic acid group. As used herein "capable to interact with the surface of the nanovesicles" includes non-covalently binding of the active agent to the nanovesicles, in particular to the surface of the nanovesicles. For example, at least 10%, at least 20%, at least 30%, at least 40%, at least 50%, at least 70%, at least 80%, or at least 90%, of the total amount of active agent interacts with the surface of the nanovesicles, the balance being dissolved in the aqueous phase.

In the context of the present specification, the expression "the formulation comprises less than or equal to 0.9% w/w of propylene glycol" is meant to include embodiments in which the formulation comprises essentially no propylene glycol.

In preferred embodiments, the formulation comprises essentially no propylene glycol.

As used herein, the expressions "essentially free of compound X", "does essentially not comprise compound X", or "comprises essentially no compound X" with respect to a formulation are interchangeable. In particular, these expressions specify that the formulation is either free of compound X or comprises less than 0.1% (w/w), less than 0.08% (w/w), less than 0.07% (w/w), less than 0.06% (w/w), less than 0.05% (w/w), less than 0.04% (w/w), less than 0.03% (w/w), less than 0.02% (w/w), or less than 0.01% (w/w) of compound X based on the total weight of the formulation.

As used herein, the expression "the composition comprises less than X % of compound X", is meant to include embodiments in which the composition is free of compound X.

The formulation may comprise less than or equal to 0.99%, 0.95%, 0.9%, 0.8%, 0.7%. 0.6%, 0.5%, 0.4%, 0.3%, 0.2%, or 0.1% w/w of propylene glycol or no propylene glycol.

In particular, the formulation may comprise less than or equal to 0.7%, 0.5%, 0.3% or 0.1% w/w of propylene glycol.

More particular, the formulation may comprise less than or equal to 0.5%, 0.3% or 0.1% w/w of propylene glycol.

Most particular, the formulation may comprise less than or equal to 0.3% or 0.1% w/w of propylene glycol.

In preferred embodiments, the formulation comprises no propylene glycol.

In addition to comprising no propylene glycol or only small amounts of propylene glycol as defined above, it is preferred that the formulation comprises no, essentially no, less than 1%, or less than or equal to 0.99%, 0.95%, 0.9%, 0.8%, 0.7%, 0.6%, 0.5%, 0.4%, 0.3%, 0.2%, or 0.1% w/w of a non-cyclic polyol having 2 to 3 carbon atoms (i.e., having not more than 3). Preferably, the formulation comprises no, essentially no, less than 1%, or less than or equal to 0.99%, 0.95%, 0.9%, 0.8%, 0.7%. 0.6%, 0.5%, 0.4%, 0.3%, 0.2%, or 0.1% w/w of a non-cyclic polyol having 2 to 4, 2 to 5, 2 to 6, 2 to 7, 2 to 8, 2 to 9 or 2 to 10 carbon atoms (i.e., having not more than 4, 5, 6, 7, 8, 9, or 10 carbon atoms, respectively). More preferably, the formulation comprises no, essentially no, less than 1%, or less than or equal to 0.99%, 0.95%, 0.9%, 0.8%, 0.7%, 0.6%, 0.5%, 0.4%, 0.3%, 0.2%, or 0.1% w/w of a polyol having 2 to 4, 2 to 5, 2 to 6, 2 to 7, 2 to 8, 2 to 9, 2 to 10, 2 to 11 or 2 to 12 carbon atoms (i.e., having not more than 4, 5, 6, 7, 8, 9, 10, 11 or 12 carbon atoms, respectively). More preferably, the formulation comprises no, essentially no, less than 1%, or less than or equal to 0.99%, 0.95%, 0.9%, 0.8%, 0.7%, 0.6%, 0.5%, 0.4%, 0.3%, 0.2%, or 0.1% w/w of a non-cyclic polyol having 2 to 15, 2 to 20, 2 to 25 or 2 to 30 carbon atoms (i.e., having not more than 15, 20, 25 or 30 carbon atoms, respectively). Even more preferably, the formulation comprises no, essentially no, less than 1%, or less than or equal to 0.99%, 0.95%, 0.9%, 0.8%, 0.7%, 0.6%, 0.5%, 0.4%, 0.3%, 0.2%, or 0.1% w/w of a polyol having 2 to 15, 2 to 20, 2 to 25 or 2 to 30 carbon atoms (i.e., having not more than 15, 20, 25 or 30 carbon atoms, respectively). Even more preferably, the formulation comprises no, essentially no, less than 1%, or less than or equal to 0.99%, 0.95%, 0.9%, 0.8%, 0.7%, 0.6%, 0.5%, 0.4%, 0.3%, 0.2%, or 0.1% w/w of a non-cyclic polyol.

"Non-cyclic polyol" in the context of the present specifications means that the polyol does not comprise any cyclic hydrocarbon moieties, in particular no cyclic sugar moieties. The non-cyclic polyol may be linear or branched. The non-cyclic polyol may be a diol, a triol or may comprise more than three OH groups.

In preferred embodiments, the formulation of the invention comprises no, essentially no or less than 0.9%, 0.8%, 0.7%. 0.6%, 0.5%, 0.4%, 0.3%, 0.2%, or 0.1% w/w of a polyol having a molecular weight of less than 100 g/mol, less than 200 g/mol, less than 300 g/mol, less than 400 g/mol, less than 500 g/mol, less than 600 g/mol, less than 700 g/mol, less than 800 g/mol, less than 900 g/mol, or less than 1000 g/mol.

The formulation of the present invention may be essentially free of glycerin.

The formulation of the present invention may be essentially free of diglycerin.

The formulation of the present invention may be essentially free of polyglycerin.

The formulation of the present invention may be essentially free of diethylene glycol.

The formulation of the present invention may be essentially free of dipropylene glycol.

The formulation of the present invention may be essentially free of butylene glycol.

The formulation of the present invention may be essentially free of pentylene glycol.

The formulation of the present invention may be essentially free of hexylene glycol.

The formulation of the present invention may be essentially free of 1,3-propanediol.

The formulation of the present invention may be essentially free of 1,5-pentanediol.

The formulation of the present invention may be essentially free of octane-1,2-diol.

The formulation of the present invention may be essentially free of polyethyleneglycols, particularly having from 2 to 50 ethylene oxide groups.

The formulation of the present invention may be essentially free of monosaccharides and disaccharides such as sorbitol, mannitol, and mixtures thereof.

The formulation of the present invention may comprise less than or equal to 0.9%, 0.8%, 0.7%, 0.6%, 0.5%, 0.4%, 0.3%, 0.2%, or 0.1% w/w of glycerin or no glycerin. This formulation may be free of a paraben, as described herein.

In particular, the formulation of the present invention may comprise less than or equal to 0.7%, 0.5%, 0.3% or 0.1% w/w of glycerin. This formulation may be free of a paraben, as described herein.

More particular, the formulation of the present invention may comprise less than or equal to 0.5%, 0.3% or 0.1% w/w of glycerin. This formulation may be free of a paraben, as described herein.

Most particular, the formulation of the present invention may comprise less than or equal to 0.3% or 0.1% w/w of glycerin. This formulation may be free of a paraben, as described herein.

The formulation of the present invention may comprise less than or equal to 0.9%, 0.8%, 0.7%, 0.6%, 0.5%, 0.4%, 0.3%, 0.2%, or 0.1% w/w of diglycerin or no diglycerin. This formulation may be free of a paraben, as described herein.

In particular, the formulation of the present invention may comprise less than or equal to 0.7%, 0.5%, 0.3% or 0.1% w/w of diglycerin. This formulation may be free of a paraben, as described herein.

More particular, the formulation of the present invention may comprise less than or equal to 0.5%, 0.3% or 0.1% w/w of diglycerin. This formulation may be free of a paraben, as described herein. Most particular, the formulation of the present invention may comprise less than or equal to 0.3% or 0.1% w/w of diglycerin. This formulation may be free of a paraben, as described herein.

The formulation of the present invention may comprise less than or equal to 0.9%, 0.8%, 0.7%, 0.6%, 0.5%, 0.4%, 0.3%, 0.2%, or 0.1% w/w of polyglycerin or no polyglycerin. This formulation may be free of a paraben, as described herein.

In particular, the formulation of the present invention may comprise less than or equal to 0.7%, 0.5%, 0.3% or 0.1% w/w of polyglycerin. This formulation may be free of a paraben, as described herein.

More particular, the formulation of the present invention may comprise less than or equal to 0.5%, 0.3% or 0.1% w/w of polyglycerin. This formulation may be free of a paraben, as described herein.

Most particular, the formulation of the present invention may comprise less than or equal to 0.3% or 0.1% w/w of polyglycerin. This formulation may be free of a paraben, as described herein.

The formulation of the present invention may comprise less than or equal to 0.9%, 0.8%, 0.7%, 0.6%, 0.5%, 0.4%, 0.3%, 0.2%, or 0.1% w/w of diethylene glycol or no diethylene glycol. This formulation may be free of a paraben, as described herein.

In particular, the formulation of the present invention may comprise less than or equal to 0.7%, 0.5%, 0.3% or 0.1% w/w of diethylene glycol. This formulation may be free of a paraben, as described herein.

More particular, the formulation of the present invention may comprise less than or equal to 0.5%, 0.3% or 0.1% w/w of diethylene glycol. This formulation may be free of a paraben, as described herein.

Most particular, the formulation of the present invention may comprise less than or equal to 0.3% or 0.1% w/w of diethylene glycol. This formulation may be free of a paraben, as described herein.

The formulation of the present invention may comprise less than or equal to 0.9%, 0.8%, 0.7%, 0.6%, 0.5%, 0.4%, 0.3%, 0.2%, or 0.1% w/w of dipropylene glycol or no dipropylene glycol. This formulation may be free of a paraben, as described herein.

In particular, the formulation of the present invention may comprise less than or equal to 0.7%, 0.5%, 0.3% or 0.1% w/w of dipropylene glycol. This formulation may be free of a paraben, as described herein.

More particular, the formulation of the present invention may comprise less than or equal to 0.5%, 0.3% or 0.1% w/w of dipropylene glycol. This formulation may be free of a paraben, as described herein.

Most particular, the formulation of the present invention may comprise less than or equal to 0.3% or 0.1% w/w of dipropylene glycol. This formulation may be free of a paraben, as described herein.

The formulation of the present invention may comprise less than or equal to 0.9%, 0.8%, 0.7%, 0.6%, 0.5%, 0.4%, 0.3%, 0.2%, or 0.1% w/w of butylene glycol or no butylene glycol. This formulation may be free of a paraben, as described herein.

In particular, the formulation of the present invention may comprise less than or equal to 0.7%, 0.5%, 0.3% or 0.1% w/w of butylene glycol. This formulation may be free of a paraben, as described herein.

More particular, the formulation of the present invention may comprise less than or equal to 0.5%, 0.3% or 0.1% w/w of butylene glycol. This formulation may be free of a paraben, as described herein.

Most particular, the formulation of the present invention may comprise less than or equal to 0.3% or 0.1% w/w of butylene glycol. This formulation may be free of a paraben, as described herein.

The formulation of the present invention may comprise less than or equal to 0.9%, 0.8%, 0.7%, 0.6%, 0.5%, 0.4%, 0.3%, 0.2%, or 0.1% w/w of pentylene glycol or no pentylene glycol. This formulation may be free of a paraben, as described herein.

In particular, the formulation of the present invention may comprise less than or equal to 0.7%, 0.5%, 0.3% or 0.1% w/w of pentylene glycol. This formulation may be free of a paraben, as described herein.

More particular, the formulation of the present invention may comprise less than or equal to 0.5%, 0.3% or 0.1% w/w of pentylene glycol. This formulation may be free of a paraben, as described herein.

Most particular, the formulation of the present invention may comprise less than or equal to 0.3% or 0.1% w/w of pentylene glycol. This formulation may be free of a paraben, as described herein.

The formulation of the present invention may comprise less than or equal to 0.9%, 0.8%, 0.7%, 0.6%, 0.5%, 0.4%, 0.3%, 0.2%, or 0.1% w/w of hexylene glycol or no hexylene glycol. This formulation may be free of a paraben, as described herein.

In particular, the formulation of the present invention may comprise less than or equal to 0.7%, 0.5%, 0.3% or 0.1% w/w of hexylene glycol. This formulation may be free of a paraben, as described herein.

More particular, the formulation of the present invention may comprise less than or equal to 0.5%, 0.3% or 0.1% w/w of hexylene glycol. This formulation may be free of a paraben, as described herein.

Most particular, the formulation of the present invention may comprise less than or equal to 0.3% or 0.1% w/w of hexylene glycol. This formulation may be free of a paraben, as described herein.

The formulation of the present invention may comprise less than or equal to 0.9%, 0.8%, 0.7%, 0.6%, 0.5%, 0.4%, 0.3%, 0.2%, or 0.1% w/w of 1,3-propanediol or no 1,3-propanediol. This formulation may be free of a paraben, as described herein.

In particular, the formulation of the present invention may comprise less than or equal to 0.7%, 0.5%, 0.3% or 0.1% w/w of 1,3-propanediol. This formulation may be free of a paraben, as described herein.

More particular, the formulation of the present invention may comprise less than or equal to 0.5%, 0.3% or 0.1% w/w of 1,3-propanediol. This formulation may be free of a paraben, as described herein.

Most particular, the formulation of the present invention may comprise less than or equal to 0.3% or 0.1% w/w of 1,3-propanediol. This formulation may be free of a paraben, as described herein.

The formulation of the present invention may comprise less than or equal to 0.9%, 0.8%, 0.7%, 0.6%, 0.5%, 0.4%, 0.3%, 0.2%, or 0.1% w/w of 1,5-pentanediol or no 1,5-pentanediol. This formulation may be free of a paraben, as described herein.

In particular, the formulation of the present invention may comprise less than or equal to 0.7%, 0.5%, 0.3% or 0.1% w/w of 1,5-pentanediol. This formulation may be free of a paraben, as described herein.

More particular, the formulation of the present invention may comprise less than or equal to 0.5%, 0.3% or 0.1% w/w of 1,5-pentanediol. This formulation may be free of a paraben, as described herein.

Most particular, the formulation of the present invention may comprise less than or equal to 0.3% or 0.1% w/w of 1,5-pentanediol. This formulation may be free of a paraben, as described herein.

The formulation of the present invention may comprise less than or equal to 0.9%, 0.8%, 0.7%, 0.6%, 0.5%, 0.4%, 0.3%, 0.2%, or 0.1% w/w of octane-1,2-diol or no octane-1,2-diol. This formulation may be free of a paraben, as described herein.

In particular, the formulation of the present invention may comprise less than or equal to 0.7%, 0.5%, 0.3% or 0.1% w/w of octane-1,2-diol. This formulation may be free of a paraben, as described herein.

More particular, the formulation of the present invention may comprise less than or equal to 0.5%, 0.3% or 0.1% w/w of octane-1,2-diol. This formulation may be free of a paraben, as described herein.

Most particular, the formulation of the present invention may comprise less than or equal to 0.3% or 0.1% w/w of octane-1,2-diol. This formulation may be free of a paraben, as described herein.

The formulation of the present invention may comprise less than or equal to 0.9%, 0.8%, 0.7%, 0.6%, 0.5%, 0.4%, 0.3%, 0.2%, or 0.1% w/w of polyethyleneglycols, particularly having from 2 to 50 ethylene oxide groups or no polyethyleneglycols. This formulation may be free of a paraben, as described herein.

In particular, the formulation of the present invention may comprise less than or equal to 0.7%, 0.5%, 0.3% or 0.1% w/w of polyethyleneglycols, particularly having from 2 to 50 ethylene oxide groups. This formulation may be free of a paraben, as described herein.

More particular, the formulation of the present invention may comprise less than or equal to 0.5%, 0.3% or 0.1% w/w of polyethyleneglycols, particularly having from 2 to 50 ethylene oxide groups. This formulation may be free of a paraben, as described herein.

Most particular, the formulation of the present invention may comprise less than or equal to 0.3% or 0.1% w/w of polyethyleneglycols, particularly having from 2 to 50 ethylene oxide groups. This formulation may be free of a paraben, as described herein.

The formulation of the present invention may comprise less than or equal to 0.9%, 0.8%, 0.7%, 0.6%, 0.5%, 0.4%, 0.3%, 0.2%, or 0.1% w/w of monosaccharides and disaccharides such as sorbitol, mannitol and mixtures thereof or no sugars such as sorbitol, mannitol and mixtures thereof. This formulation may be free of a paraben, as described herein.

In particular, the formulation of the present invention may comprise less than or equal to 0.7%, 0.5%, 0.3% or 0.1% w/w of monosaccharides and disaccharides such as sorbitol, mannitol and mixtures thereof. This formulation may be free of a paraben, as described herein.

More particular, the formulation of the present invention may comprise less than or equal to 0.5%, 0.3% or 0.1% w/w of monosaccharides and disaccharides such as sorbitol, mannitol and mixtures thereof. This formulation may be free of a paraben, as described herein.

Most particular, the formulation of the present invention may comprise less than or equal to 0.3% or 0.1% w/w of monosaccharides and disaccharides such as sorbitol, mannitol and mixtures thereof. This formulation may be free of a paraben, as described herein.

The formulation of the present invention may be free of, may be essentially free of, or may comprise less than an indicated amount, such as less than 1%, less than 0.99%, less than 0.95%, less than 0.9%, less than 0.8%, less than 0.7%, less than 0.6%, less than 0.5%. less than 0.4%, less than 0.3%, less than 0.2% or less than 0.1% of one polyol, all polyols or any chosen number of polyols selected from the group consisting of glycerin, diglycerin, polyglycerin, diethylene glycol, propylene glycol, dipropylene glycol, butylene glycol, pentylene glycol, hexylene glycol, 1,3-propanediol, 1,5-pentanediol, octane-1,2-diol, polyethyleneglycols, particularly having from 2 to 50 ethylene oxide groups, and monosaccharides or disaccharides such as sorbitol, mannitol and mixtures thereof. The formulation of the present invention may be essentially free of one polyol or any chosen number of polyols selected from the group consisting of glycerin, diglycerin, polyglycerin, diethylene glycol, propylene glycol, dipropylene glycol, butylene glycol, pentylene glycol, hexylene glycol, 1,3-propanediol, 1,5-pentanediol, octane-1,2-diol, polyethyleneglycols, particularly having from 2 to 50 ethylene oxide groups, and monosaccharides or disaccharides such as sorbitol, mannitol and mixtures thereof, but may comprise another polyol. The formulation of the present invention may be essentially free of a polyol which is linear or branched, but non-cyclic. The formulation of the present invention may be essentially free of a polyol having a carbon atom number of 2 to 30, more preferably 2 to 20, even more preferably 2 to 10 or 2 to 8, most preferably 2 to 6 or 2 to 3.

The formulation may comprise less than or equal to 0.99%, 0.95%, 0.9%, 0.8%, 0.7%, 0.6%, 0.5%, 0.4%, 0.3%, 0.2%, or 0.1% w/w of a polyol or no polyol. The polyol may be a polyol as described herein.

The formulation may comprise less than or equal to 0.7%, 0.5%, 0.3% or 0.1% w/w of a polyol. The polyol may be a polyol as described herein.

The formulation may comprise less than or equal to 0.5%, 0.3% or 0.1% w/w of a polyol. The polyol may be a polyol as described herein.

The formulation may comprise less than or equal to 0.3% or 0.1% w/w of a polyol. The polyol may be a polyol as described herein.

The formulation may comprise no polyol.

The small size of the nanovesicles and their high homogeneity confers on them advantageous properties which distinguish them from conventional emulsions: The nanoemulsions and formulations comprising nanoemulsions of the present invention are transparent. Further, the nanoemulsion and formulations comprising nanoemulsions of the present invention can carry active agents more efficiently and, thus, become increasingly important in the field of medicine and pharmacy.

"Aging" as used herein, refers to alteration, disintegration and/or degradation of the formulation, affecting chemical and physical stability during storage, in particular under stressed conditions. Such physical or chemical changes due to storage may include, but are not limited to Ostwald ripening, flocculation, coalescence and/or breaking, which may lead to a change in vesicle size or polydispersity index. "Aging" as used herein, may include the formation of impurities after storage, for example for 6 months at 25° C. or 40° C. Typical impurities of formulations comprising 5-aminolevulinic acid as active agent are 2-hydroxypropyl-δ-aminolevulinate and an impurity characterized by m/z=246.

The inventors have found that the formulations of the present invention are surprisingly stable and resistant to aging. In particular, the formulations of the present invention comprise fewer impurities than prior art formulations, even after storage, for example for 6 months at 25° C. or 40° C.

As used herein, "stressed conditions" for storage are temperatures significantly exceeding room temperature (e.g., 40° C.).

As used herein, a "nanovesicle emulsion" or a "nanoemulsion" is a dispersion of oil in water (oil-in-water dispersion, oil-in-water emulsion, O/W emulsion). The nanoemulsion can be monophasic, transparent and/or slightly opalescent. The nanoemulsions of the present invention can be colloidal systems, which include dispersed nanovesicles comprising a lipid core surrounded by at least one surfactant or emulsifier monolayers. The nanoemulsions and the formulations comprising the nanoemulsions of the present invention are characterized by a mean particle or nanovesicle size of less than 500 nm less, than 200 nm, or less than 100 nm. The nanoemulsions and the formulations comprising the nanoemulsions of the present invention has a narrow (homogeneous) nanovesicle size distribution, for example a nanovesicle size distribution characterized by a polydispersity index of less than or equal to 0.4.

As used herein, "nanovesicle", "nano vesicle", "lipid vesicles", "oil droplets", "droplets" and "oil globules" are interchangeable and refer to small oil droplets in an oil in water emulsion. A lipid vesicle of an average size (see above, e.g., below 500, 200, 100 nm) that is compiled of a monolayer of a surfactant and a lipid core. In the present invention, the nanovesicles can have a size of less than or equal to 500 nm, or less than or equal to 300 nm, preferably in the range of 5 nm to 200 nm, more preferably in the range of 5 nm to 100 nm.

As used herein, the term "nanoparticle" or "nano particle", is distinguished form "nanovesicles", and refers to solid particles, which are not described in this invention. The formulation of the present invention may be a formulation which is essentially free of nanoparticles. "Essentially free of nanoparticles" means, that the formulation comprises less than or equal to 2% by weight, or less than or equal to 1% by weight of, or does not comprise nanoparticles. Nanoparticles are mainly inorganic, solid lipids or polymeric solid particles may have a size of below 100 nm, below 200 nm, or below 500. The size can be determined by the methods as described herein. For example, the formulation may be essentially free of nanoparticles with a diameter of less than 100 nm, as determined by dynamic light scattering.

As used herein, "topical use" of the formulation of the invention describes an application to a particular place on or in the body, in particular the human body. This includes, but is not limited to administration of the formulation to body surfaces such as the skin or mucous membranes. The topical use can be epicutaneous, meaning that the formulation is directly administered to the skin. In particular the topical use is a pharmaceutical use.

As used herein, the "stability" of a formulation comprising nanovesicles, as described herein, includes, but is not limited to the physical and chemical stability. In particular, in the present invention, a formulation is stable if the integrity of the nanovesicles is found to be stable. A measure known to the skilled person to describe integrity of the nanovesicles is the size, as for example determined by dynamic light scattering, as described herein. The nanovesicles produced according to the invention can have a size below 100 nm, preferably below 50 nm, more preferably in the range of 20-30 nm, immediately after manufacture. For example, the formulation as described herein is stable if the nanovesicles in the formulation of the present invention have a size (or diameter) of less than or equal to 500 nm or less than or equal to 300 nm, preferably in the range of 5 nm to 200 nm, more preferably in the range of 5 nm to 100 nm.

"Stability" can also refer to the absence of processes above described as aging, leading to a loss of pharmaceutical functionality or quality. The composition described in this invention is functional or pharmaceutically functional, as long as the vesicle size is less than or equal to 500 nm or less than or equal to 300 nm, preferably in the range of 5 nm to 200 nm, more preferably in the range of 5 nm to 100 nm.

Furthermore, "stability" can refer to the stable content of the hydrophilic active compound, in particular 5-ALA. During storage, the content of 5-ALA is, for example, considered stable if at least 70%, at least 80% or at least 90% of the content of the active agent is still present, when stored, for example, at stressed conditions, as described herein.

In a formulation of the invention, the 5-ALA content may be
(i) at least 95% after storage for 3 months at 40° C., and/or
(ii) at least 95% or at least 97% after storage for 3, 6, 9 or 12 months at 25° C., and/or
(iii) at least 95%, at least 97% or at least 99% after storage for 12, 18, 24 or 36 months at 5° C.

As used herein "stability" of the compositions also refers to a low content of impurities to a small amount of impurities. For example, the formulation of the invention is stable if it contains an entity of m/z=246 in an amount of less than or equal to 1.5%, 1.0% or 0.75% when stored for 6 months at 40° C., or in an amount of less than or equal to 0.5%, 0.4%, 0.3% or 0.2% when stored for 6 months at 25° C.

In the present invention, the formulation can be stable for at least one month, at least 3 months, at least 6 months, at least 9 months, at least 12 months, e.g., at room temperature (e.g., 15-25° C.). In particular, the formulation of the invention can be stable for at least one month, at least 3 months, at least 6 months, at least 9 months, at least 12 months, at least 24 months, or at least 36 months, at 2-8° C., or at about 5° C.

The formulation of the present invention may have a nanovesicle size of less than or equal to 500 nm, or less than or equal to 300 nm, or less than or equal to 200 nm, preferably in the range of 5 nm to 200 nm, more preferably in the range of 5 nm to 150 nm, when stored for one month at 40° C.

The formulation of the present invention may have a nanovesicle size of less than or equal to 500 nm, or less than or equal to 300 nm, or less than or equal to 200 nm, preferably in the range of 5 nm to 200 nm, when stored for six months at 25° C.

The size or diameter of the nanovesicles as described herein can be expressed as the Z-average (also termed "z-average"). The size distribution of the nanovesicles can be characterized by the polydispersity index. These parameters are well known to the skilled person, and are widely used in the art to characterize particle or vesicles in emulsions, suspensions and/or polymeric solutions.

In the present invention, the size of the nanovesicles (e.g., z-average in nm) and/or the heterogeneity of nanovesicle formulations (characterized by the polydispersity index) can be determined by dynamic light scattering (also referred as Photon Correlation Spectroscopy (PCS) or Quasi-Elastic Light Scattering (QELS)). Dynamic light scattering is well known in the art and well established to determine size of nano or micro particles or vesicles in emulsions, suspensions and/or polymeric solutions with a laser.

In the formulation as described herein, the total aqueous component can present in an amount of 50% to 99% w/w, based on the total weight of the nanoemulsion (a), preferably from 70% to 95% (w/w), and more preferably from 75% to 95% (w/w), or 80% to 95%.

As used herein, "weight per weight", "weight/weight" or "w/w" means the weight concentration or mass concentration of a component in a formulation described herein. The weight or mass of a component is expressed as a percentage of a reference formulation. For example, the weight or mass of a component can be expressed as a percentage of the total weight or mass of the formulation of the invention, or as a percentage of the total weight or mass of the nanoemulsion (a).

The aqueous component can comprise at least one pH buffering agent. Any suitable buffering agent may be used. Suitable buffering agents are known to the skilled person.

For example, the at least one pH buffering agent can be selected from the group consisting of citrate, phosphate, acetate and carbonate.

The pH of the aqueous component can be in the range of 2-9. The pH of the aqueous component can also be preferably in the range of 2-6, such as 2, 3, 4, 5 or 6, more preferably in the range of 4-6, such as 4, 5 or 6, or 2-4, such as 2, 3 or 4.

In the formulation as described herein, the at least one lipophilic component can be selected from triglycerides and mixtures thereof.

Preferably, the at least one lipophilic component is a lipid, a synthetic oil, a vegetable oil and/or an animal oil. Suitable lipids according to the present invention are physiologically acceptable lipids such as ceramide, mono-, di- and triacylglycerin (triglycerides). In particular, the at least one lipophilic component is a triglyceride, preferably a triglyceride comprising a $C_{8-10}$ fatty acid, or a mixture thereof. More particular, the at least one lipophilic component is a caprylic and/or capric triglyceride and/or a mixture thereof, particularly preferably Miglyol (such as Miglyol 812, available e.g., from IOI Oleochemical) or Myritol (such as Myritol 318, available e.g., from BASF). Suitable vegetable and animal oils e.g., are sunflower oil, soybean oil, peanut oil, rape oil, fish oil and/or cetaceum.

In the formulation as described herein, the at least one lipophilic component can be present in an amount of from 0.1% to 30% (w/w) based on the total weight of the nanoemulsion (a), preferably from 0.25% to 15% (w/w), preferably from 0.25% to 10% (w/w), and more preferably from 0.5% to 8% (w/w) or 3% to 8% (w/w). Also preferred is the at least one lipophilic component being present in an amount of from 10% to 30% (w/w) based on the total weight of the nanoemulsion (a), more preferably 15-30%, or 10-20%.

In the formulation as described herein, a triglyceride or triglycerides can be present in an amount of from 2% to 10% (w/w), based on the total weight of nanoemulsion (a), preferably from 3% to 8% (w/w).

In the formulation as described herein, the at least one surfactant may be any suitable surfactant known to the skilled person.

Surfactants, also referred as surface active agents or emulsifiers, are well-known in the art and include any agent linking oil and water in the composition to form an emulsion. They lower the surface tension of two liquids and are amphiphilic. In emulsions they are referred as emulsifiers and coat the droplets preventing coalescing. Emulsifiers can be described with the hydrophilic/lipophilic balance (HLB), which expresses their affinity towards water or oil. Low HLB (e.g., HLB=1) refers to lipophilic emulsifiers and high (e.g., HLB=20) to hydrophilic emulsifiers. In general, lipophilic emulsifiers are used for water-in-oil emulsions and hydrophilic emulsifiers for oil-in-water emulsions. Persons skilled in the art will identify which emulsifiers or mixtures of them are suited for the preferred vehicles and purpose of the composition. In certain emulsions, combinations of emulsifiers might be advantageous.

A suitable membrane-forming surfactant is a phospholipid, a lysophospholipid, a ceramide and/or a mixture thereof. Preferably, the phospholipid is lecithin or cephalin from soybeans or hens' eggs. More preferably the at least one surfactant is lecithin, most preferably soy lecithin.

In the formulation as described herein, the phospholipid, the lysophospholipid, the ceramide and/or the mixture thereof can be present in an amount of from 0.1% to 10% (w/w), based on the total weight of nanoemulsion (a), preferably from 0.15% to 5% (w/w), more preferably from 1% to 5% and even more preferably from 0.2% to 3% (w/w).

Preferably, the lecithin has a phosphatidylcholine content of at least 80% by weight, more preferably of at least 90% by weight, and most preferably of at least 94% by weight. The quality of the lecithin, namely its phosphatidylcholine content, plays a crucial role for the size of the vesicles of the nanoemulsion. The higher the phosphatidylcholine content of the lecithin, the smaller is the size of the vesicles of the nanoemulsion.

As O/W emulsion-forming surfactant, anionic, nonionic, cationic and/or amphoteric surfactants are suitable as well as block copolymers. Suitable anionic surfactants are soaps, alkylbenzene sulphonates, alkane sulphonates, alkylsulfates and/or alkyl ether sulfates. Suitable cationic surfactants are quaternary ammonium compounds, preferably having one or two hydrophobic groups (e.g., cetyltrimethylammonium bromide and cetyltrimethylammonium chloride) and/or salts of tong-chain primary amines. A suitable amphoteric surfactant is N-(acylamidoalkyl) betaine, N-alkyl-β-aminopropionate, phosphate-alkyl-ammonium compounds, and/or amine-N-oxide. A suitable copolymer building block, for example, is propylene oxide. In the present invention, a nonionic surfactant is particularly preferred as O/W emulsion-forming surfactant.

In the formulation as described herein, the at least one surfactant can be any a polyoxyethylene-type surfactant. A suitable nonionic surfactant can be selected from the group consisting of fatty alcohol polyglycolether, alkylphenol polyglycolether, alkylpolyglucoside, fatty acid glucamide, fatty acid polyglycolether, ethylen oxide-propylene oxide-block polymer, polyglycerol fatty acid ester, fatty acid alcanolamide and (ethoxylated) sorbitane fatty acid ester (sorbitane). A particularly preferred ethoxylated sorbitane fatty acid ester is polyoxyethylene sorbitane monooleate, most preferably Polysorbate 80.

The at least one surfactant, such as the polyoxyethylene-type surfactant, can be present in an amount of from 0.1% to 10% (w/w), based on the total weight of the nanoemulsion (a), more preferably from 2% to 10% (w/w), even more preferably from 0.2% to 5% (w/w), and most preferably from 1% to 5% (w/w) or 0.5% to 5% (w/w).

The formulation of the invention can comprise as least one hydrophilic surfactant with an HLB of 9 to 17, more preferably 12-16, particularly polysorbate 80 to form a nanoemulsion.

The at least one surfactant can be a sugar-based surfactant. Sugar-based surfactants are a group of non-ionic surfactants using hydrophilic sugars to which hydrophobic tails are bound. One common substance of this class is n-dodecyl-β-D-maltoside, a member of the maltoside surfactants so named because the sugar unit used is maltose. An example of a pyranoside surfactant is n-octyl-β-D-thioglucopyranoside. This class uses pyranose as the sugar unit. Examples of the glycoside surfactants are octyl glucoside, decyl glucoside, and lauryl glucoside. An example of a polysugar surfactant is digitonin.

Another very important group of sugar-based surfactants are the Tween surfactants, most notable Tween 20 (also termed herein Polysorbate 20) and Tween 80 (also termed herein Polysorbate 80). These surfactants are based on a sorbitan sugar, which is why they are commonly referred to as polysorbate surfactants. Three oligo (ethylene glycol) side groups of varying lengths are bound to the sugar increasing the hydrophilicity of the head group. This structure forms the core of all Tween surfactants. They deviate in the hydrophobic tail, which is a fatty acid coupled via an ester to four oligo (ethylene glycol) tail. In Tween 20 this fatty acid is lauric acid; in Tween 80 it is oleic acid.

In preferred embodiments, the at least one alcohol comprises at least three carbon atoms.

In the formulation as described herein, the at least one alcohol preferably independently has 3-5 (i.e. no more than 5) or 3-4 (i.e. no more than 4) carbon atoms. The at least one alcohol can be at least one monohydric alcohol. Particularly suitable alcohols having 5 carbon atoms are 1-pentanol and/or 4-methyl-2-pentanol. Suitable alcohols having 4 carbon atoms are 1-butyl alcohol, iso-butyl alcohol (2-methyl-1-propanol), tert-butyl alcohol (2-methyl-2-propanol) and/or sec-butyl alcohol (2-butanol). The alcohol is not propylene glycol.

Preferably, the at least one alcohol has 3 carbon atoms, i.e. is selected from the group consisting of 1-propanol or 2-propanol (isopropyl alcohol) and mixtures thereof. A preferred alcohol is 2-propanol.

In the formulation as described herein, the alcohol may present in an amount of from 0.1% to 10% w/w based on the total weight of the nanoemulsion (a), preferably from 1% to 5% (w/w) or 0.5% to 5% (w/w), and more preferably from 1% to 2% (w/w).

The formulation as described herein may comprise a gelling agent. Any suitable gelling agent may be used. Suitable gelling agents and mixtures thereof are known to the skilled person. In the formulation as described herein, the gelling agent may be selected from the group consisting of poloxamer, xanthan, bentonite, sodium carboxymethylcellulose, hydroxymethyl cellulose, carbomer, hydroxypropyl cellulose, gellan gum, guar gum, pectin, poly(ethylene) oxide, polycarbophil, alginate, tragacanth, povidone, gelatin, and mixtures thereof.

It is preferred that the gelling agent is selected from poloxamer, xanthan and/or mixtures thereof.

It is also preferred that the gelling agent is xanthan (xanthan gum).

It is also preferred that the gelling agent is a poloxamer.

Poloxamers are nonionic triblock copolymers composed of a central hydrophobic chain of polyoxypropylene (poly (propylene oxide)) flanked by two hydrophilic chains of polyoxyethylene (poly(ethylene oxide)). Commercially available are Poloxamer 407 and Poloxamer 188. Poloxamer 407 can have an average molecular weight of about 12600 Dalton. Poloxamer 188 can have an average molecular weight of about 8400 Dalton. In the formulation as described herein, a preferred poloxamer is Poloxamer 407.

In the formulation as described herein, the gelling agent may be present in an amount of from 0.1% to 10% (w/w), based on the total weight of the formulation, preferably from 0.25% to 5% (w/w), and more preferably from 0.5% to 4% (w/w) or 1% to 4% (w/w).

The formulation as described herein may comprise a preservative. Any suitable preservative may be used. Suitable preservatives are known to the skilled person. The preservative can be selected from benzoate, citric acid, EDTA, potassium sorbate, vitamin C and/or derivatives and any mixtures thereof, wherein the preservative is preferably sodium benzoate. Suitable aqueous mixtures of sodium benzoate and potassium sorbate are commercially available, for example Euxyl™ K 712 preservative (Ashland).

The preservative can be present in the formulation as described herein in an amount of from 0.01% to 3% (w/w) based on the total weight of the formulation, preferably from 0.2% to 2% (w/w) or 0.1-2% (w/w), and more preferably from 0.2% to 1.5% (w/w).

In particular, the formulation of the present invention is essentially free of parabens, preferably free of parabens. The class of paraben compounds include p-hydroxybenzoates and PHB esters (esters of p-hydroxybenzoic acid, also known as 4-hydroxybenzoic acid).

Parabens are only slightly soluble in water. In the preparation of an aqueous formulation or a formulation comprising an aqueous component, parabens must be dissolved in a solvent suitable to introduce the parabens in the aqueous phase. A suitable solvent may be a polyol, in particular propylene glycol (1,2-propanediol). In the present invention, this preparation of a solution of a paraben in propylene glycol is not needed, so the formulation of the present invention can be free of a polyol, and/or a mixture of two or more polyols, such as propylene glycol.

The formulation of the present invention can be essentially free of a polyol and/or a mixture of two or more polyols, and a paraben, preferably free of propylene glycol and a paraben.

The formulation of the present invention may be a gel formulation. As used herein, a "gel" is a two-phase elastic colloidal material, consisting of a dispersed liquid incorporated in the solid phase often constituted by a gelling agent. Suitable gelling agents, such as xanthan, are described herein.

The formulation of the present invention may be provided in a container or dispenser. Suitable dispensers and containers are known to the skilled person. For example, the dispenser may be a squeeze tube, comprising the formulation as described herein. The squeeze tube may contain the gel formulation as described herein. The dispenser may also be a metered dose dispenser or a foam dispenser or spray dispenser.

The container or dispenser may comprise a propellant, wherein the propellant is provided to pressurize the container or dispenser. Any suitable propellant may be used. Suitable propellants and mixtures thereof are known to the skilled person. Preferably, the propellant is selected from propane, isobutane, n-butane and mixtures thereof.

The formulation of the present invention may be prepared as a foamable formulation.

The formulation of the present invention may be prepared as a pressurized formulation, wherein a propellant is provided to pressurize the formulation. Any propellant as described herein can be used.

The formulation of the present invention may be prepared as a pressurized, foamable formulation, wherein a propellant is provided to pressurize the formulation. Any propellant as described herein can be used.

The formulation of the invention may be provided in a foam dispenser, as described herein, The foam dispenser comprises a container, wherein said container comprises the formulation as described herein, and a propellant. The propellant is provided to pressurize the foam dispenser. Any suitable propellant may be used, as described herein. A foam-generating device is mounted on the container. In particular, the formulation is prepared as a foamable formulation.

The invention also provides a foam, comprising the formulation of the present invention, as described herein.

In preferred embodiments, the active agent in the formulation of the invention comprises at least one carboxylic acid group, capable of undergoing esterification reactions. Preferably, the active agent is a small molecule containing a carboxylic acid group, having a molecular weight of 50 to 1000 g/mol, more preferably a molecular weight of 50 to 900 g/mol, most preferably from 100 to 850 g/mol.

The active agent may be present in an amount of from 0.001% to 50% w/w, based on the total weight of the formulation. In particular, the active agent may be present in an amount of from 0.01% to 30% w/w, based on the total weight of the formulation, or 0.1% to 25% w/w, 0.5% to 25% w/w, 1% to 25% w/w, or 5% to 25% w/w, based on the total weight of the formulation.

In particular the active agent in the formulation of the invention is a hydrophilic compound, which has one carboxylic acid group. The active agent may be a photosensitizer or a metabolic precursor thereof, most preferably 5-aminolevulinic acid (also termed herein "ALA" or "5-ALA"), a pharmaceutically acceptable salt, a derivative, precursor and/or metabolite thereof. A preferred salt of 5-aminolevulinic acid is 5-aminolevulinic acid hydrochloride. Another preferred salt of 5-aminolevulinic acid is 5-aminolevulinic acid phosphate. 5-Aminolevulinic acid has the following chemical structure:

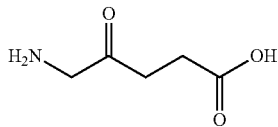

Molecular Weight: 131, 13 g/mol

5-Aminolevulinic acid is a hydrophilic agent, which may interact with the surface of the nanovesicles when dissolved in the aqueous phase.

5-Aminolevulinic acid, a pharmaceutically acceptable salt, a derivative, precursor and/or metabolite thereof may be present in an amount of from 0.001% to 50% w/w, based on the total weight of the formulation. In particular, 5-Aminolevulinic acid, a pharmaceutically acceptable salt, a derivative, precursor and/or metabolite thereof may be present in an amount of from 0.01% to 30% w/w, based on the total weight of the formulation, or 0.1% to 25% w/w, 0.5% to 25% w/w, 1% to 25% w/w, or 5% to 25% w/w, based on the total weight of the formulation.

In particular, the formulation of the present invention may comprise or consist of:
(a) a nanoemulsion comprising
  (i) an aqueous component, present in an amount of 70% to 95% w/w, based on the total weight of the nanoemulsion (a).
  (ii) nanovesicles, comprising
    (1) 1-5% of at least one phospholipid, based on the total weight of the nanoemulsion (a);
    (2) 2-10% of at least one polyoxyethylene-type surfactant, based on the total weight of the nanoemulsion (a);
    (3) 1-5% $C_3$ to $C_5$ alcohol, based on the total weight of the nanoemulsion (a); and (4) 2-10% triglycerides, based on the total weight of the nanoemulsion (a);
(b) 0.1-20% of an active agent, preferably an active agent comprising a carboxylic acid group, based on the total weight of the formulation; and
(c) 0.1-2% of at least one preservative, based on the total weight of the formulation;
wherein the formulation comprises essentially no propylene glycol, and wherein the formulation preferably has a pH of 2-4. Preferably, the formulation can comprise two surfactants, more preferably soy lecithin and Polysorbate 80.

In this formulation, the at least one phospholipid, the at least one polyoxyethylene-type surfactant, the $C_3$ to $C_5$ alcohol, the triglycerides, and the at least one preservative may be independently selected according to the herein-described disclosure.

In particular, the formulation of the present invention may comprise, essentially consist of or consist of:
(a) an emulsion of nanovesicles comprising
  (i) an aqueous component, present in an amount of 70% to 95% w/w, based on the total weight of the nanoemulsion (a).
  (ii) nanovesicles, comprising
    (1) 1-5% of at least one phospholipid, based on the total weight of the nanoemulsion (a);
    (2) 2-10% of at least one polyoxyethylene-type surfactant, based on the total weight of the nanoemulsion (a);
    (3) 1-5% $C_3$ to $C_5$ alcohol, based on the total weight of the nanoemulsion (a); and (4) 2-10% triglycerides, based on the total weight of the nanoemulsion (a);
(b) 0.1-20% of an active agent, preferably a hydrophilic active agent, preferably a photosensitizer or a metabolic precursor thereof, most preferably 5-aminolevulinic acid hydrochloride, based on the total weight of the formulation;
(c) 0.1-2% of at least one preservative, based on the total weight of the formulation; and
wherein the formulation essentially does not comprise propylene glycol, and wherein the formulation preferably has a pH of 2-4.

Preferably, the formulation can comprise two surfactants, more preferably soy lecithin and Polysorbate 80.

In this formulation, the at least one phospholipid, the at least one polyoxyethylene-type surfactant, the $C_3$ to $C_5$ alcohol, the triglycerides, and the at least one preservative may be independently selected according to the herein-described disclosure.

The present invention also relates to a nanovesicle, comprising, essentially consisting of or consisting of
(i) 16-19% w/w of soy lecithin,
(ii) 32-36% w/w of Polysorbate 80,
(iii) 32-36% w/w of caprylic/capric triglycerides, and
(iv) 12-16% w/w of isopropyl alcohol.

A preferred nanovesicle of the invention comprises essentially consists of or consists of
(i) 17% w/w of soy lecithin
(ii) 34% w/w of Polysorbate 80
(iii) 35% w/w of caprylic/capric triglycerides
(iv) 14% w/w of isopropyl alcohol.

The present invention also relates to a nanoemulsion, comprising, essentially consisting of or consisting of
(a) 1.6-3.6% w/w of soy lecithin
(b) 3.3-6.9% w/w of Polysorbate 80
(c) 3.3-7.0% w/w of caprylic/capric triglycerides
(d) 1.3-2.9% w/w of isopropyl alcohol
(e) aqueous phosphate buffer, for example aqueous 5-20 mM phosphate buffer, pH 2-8, preferably pH 2-7, more preferably pH 3-6, ad 100%.

A preferred nanoemulsion of the present invention comprises, essentially consists of or consists of:
(a) 1.7% w/w of soy lecithin
(b) 3.4% w/w of Polysorbate 80
(c) 3.5% w/w of caprylic/capric triglycerides
(d) 1.4% w/w of isopropyl alcohol
(e) aqueous 10 mM phosphate buffer, pH 6, ad 100%.

This formulation is termed herein "BF200". The BF200 nanoemulsion can be obtained by contacting a mixture of ingredients (a)-(d) in a total amount of 10% w/w and 90% w/w of an aqueous 10 mM phosphate buffer, pH 6, under condition allowing formation of a nanoemulsion, thereby forming the nanoemulsion. An exemplary method for manufacture of the BF200 formulation is described in Example 1.

Another preferred nanoemulsion of the present invention comprises, essentially consists of or consists of:
  (a) 2-3% w/w of soy lecithin
  (b) 4.5-5.5% w/w of Polysorbate 80
  (c) 4.5-5.5% w/w of caprylic/capric triglycerides
  (d) 2-3% w/w of isopropyl alcohol
  (e) aqueous 10 mM phosphate buffer, pH 6 or less, ad 100%.

This formulation is termed herein "BF215". The BF215 nanoemulsion can be obtained by contacting a mixture of ingredients (a)-(d) in a total amount of 15% w/w and 85% w/w of an aqueous 10 mM phosphate buffer, pH 6, under condition allowing formation of a nanoemulsion, thereby forming the nanoemulsion. An exemplary method for manufacture of the BF215 formulation is described in Example 1.

Yet another preferred nanoemulsion of the present invention comprises, essentially consists of or consists of:
  (a) 3-4% w/w of soy lecithin
  (b) 6-7% w/w of Polysorbate 80
  (c) 6-8% w/w of caprylic/capric triglycerides
  (d) 2-4% w/w of isopropyl alcohol
  (e) aqueous 10 mM phosphate buffer, pH 6, ad 100%.

This formulation is termed herein "BF220". The BF220 nanoemulsion can be obtained by contacting a mixture of ingredients (a)-(d) in a total amount of 20% w/w and 80% w/w of an aqueous 10 mM phosphate buffer, pH 6, under condition allowing formation of a nanoemulsion, thereby forming the nanoemulsion. An exemplary method for manufacture of the BF220 formulation is described in Example 1.

A preferred formulation of the present invention being essentially free of propylene glycol, comprises, essentially consists of or consists of:
  (1) 17.5% w/w of nanoemulsions BF200, as described herein
  (2) 2.9% w/w Xanthan,
  (3) 0.24% w/w sodium benzoate,
  (4) 10% w/w 5-ALA hydrochloride, and
  (5) water, ad 100%

This formulation may have a pH of 2-3. Preparation of this formulation is described in Example 3.

An exemplary comparative formulation, not covered by the claims, can comprise, essentially consist of or consist of:
  (1) 17.5% w/w nanoemulsions BF200, as described herein
  (2) 2.9% w/w Xanthan,
  (3) 1% w/w propylene glycol,
  (4) 0.24% w/w sodium benzoate,
  (5) 10% w/w 5-ALA hydrochloride, and
  (6) water, ad 100%

This formulation may have a pH of 2-3. Preparation of this formulation is described in Example 2.

All definitions and embodiments described for the first aspect are also envisioned for all other aspects described herein, where applicable.

Yet another aspect of the present invention relates to the formulations, as described herein, for use in medicine.

Yet another aspect of the present invention relates to the formulations as described herein, for use in a method of treatment and/or prevention of a dermatological disease or condition in a subject.

The treatment and/or prevention of the dermatological disease or condition may also comprise:
  (a) topically administering to the subject, a pharmaceutically effective amount of the formulation comprising a photosensitizer or a metabolic precursor thereof, preferably 5-aminolevulinic acid, a pharmaceutically acceptable salt, a derivative, precursor and/or metabolite thereof, as described herein, to a diseased or affected area and optionally an area surrounding the diseased or affected area of the skin, and
  (b) optionally incubating the pharmaceutically formulation on the skin of the subject with or without occlusion of the area of the skin to which the formulation was administered, the occlusion preferably performed using low density polyethylene or polyurethane film, to enhance deep layer tissue penetration.

The treatment and/or prevention of the dermatological disease or condition may also comprise:
  (a) topically administering to the subject, a pharmaceutically effective amount of the formulation comprising a photosensitizer or a metabolic precursor thereof, preferably 5-aminolevulinic acid, a pharmaceutically acceptable salt, a derivative, precursor and/or metabolite thereof, as described herein, to a diseased or affected area and optionally an area surrounding the diseased or affected area of the skin, and
  (b) optionally incubating the pharmaceutically formulation on the skin of the subject with or without occlusion of the area of the skin to which the formulation was administered, the occlusion preferably performed using low density polyethylene or polyurethane film, to enhance deep layer tissue penetration, and
  (c) irradiating the skin area to which the formulation was administered with light.

The light spectrum used for irradiation in step (c) may match the absorption spectrum of a fluorescent porphyrin. For example, the light spectrum may match the absorption peaks of protoporphyrin IX. In particular, the light used for irradiation in step (c) may comprise any visible wavelength in the range of 380 nm to 780 nm, preferably with equal irradiance throughout or irradiance peak(s) at around 410 nm and/or 505 nm and/or 542 nm and/or 575 nm and/or 635 nm. The wavelength spectrum may be essentially free of radiation with a wavelength of less than 380 nm and/or larger than 780 nm. In particular, the light used for irradiation in step (c) may comprise any visible wavelength in the range of 380-440 nm and/or 580-650 nm. The light used for irradiation in step (c) may further be capable to induce red fluorescence of accumulated porphyrins.

The light used in step (c) may be red light, blue light, green light and/or violet light, preferably red light and/or violet light, more preferably wherein (a) the red light results in a radiant exposure of 10-75 $J/cm^2$, preferably of 25-45 $J/cm^2$; and/or the violet light results in a radiant exposure of 1-30 $J/cm^2$, preferably 5 to 15 $J/cm^2$.

Irradiation in step (c) may be performed with sunlight and/or daylight or with an artificial light source emitting light with a wavelength spectrum and preferably also irradiance similar or identical to sun light. The light with a wavelength spectrum and preferably also irradiance similar or identical to sun light may have a wavelength spectrum of 100 nm to 1000 nm, a wavelength spectrum of 380 nm to 780 nm, preferably with equal irradiance throughout or irradiance peak(s) at around 410 and/or 505 and/or 635 nm, or a wavelength spectrum of 570 nm to 650 nm or 570 nm to 630 nm, and/or a wavelength spectrum of 380 nm to 440 nm. Artificial light may be provided by an LED. A suitable device providing artificial light is described, for example, in U.S. Pat. No. 11,235,169 B1 and U.S. Pat. No. 11,219,781 B2, the disclosure of which is incorporated herein by reference.

The area surrounding the diseased or affected area of the skin may include a surrounding area not affected, to ensure that the diseased or affected area is adequately treated in the peripheral diseased or affected areas. For example, the area surrounding the diseased or affected area of the skin may include an area of at least about 5 mm width.

The dermatological disease or condition to be treated with the formulation as described herein, may include, but is not limited to, diseases or conditions of the skin, skin appendages or mucosa.

The dermatological disease or condition to be treated with the formulation as described herein, may be selected from the group consisting of inflammatory, neoplastic, proliferative, infectious, and/or autoimmune diseases or conditions, and/or the cutaneous manifestation thereof, and/or diseases associated with single lesions or fields of lesions, neoplastic, proliferative and/or inflammatory changes.

The inflammatory dermatological disease or condition to be treated with the formulation as described herein, may be selected from the group consisting of dermatitis, contact dermatitis, acne, atopic dermatitis, eczema, pustular dermatitis, seborrheic dermatitis, perioral dermatitis, chronic wound, urticaria, skin ulcer, rosacea, rash, drug eruptions, toxic epidermal necrolysis; erythema multiforme, erythema nodosum, granuloma annulare, and other cutaneous manifestations of inflammation.

The neoplastic and/or proliferative dermatological disease or condition to be treated with the formulation as described herein, may be selected from the group consisting of basal cell carcinoma, preferably superficial basal cell carcinoma or nodular basal cell carcinoma; squamous cell carcinoma, preferably Morbus Bowen or invasive squamous cell carcinoma; vulvar intraepithelial neoplasia (VIN); cutaneous T-cell lymphoma; Merkel cell carcinoma; hemangioma; a nodular or subcutaneous cancer disease; field cancerization; non-melanoma skin cancer in organ transplant recipients; and prevention of non-melanoma skin cancer in organ transplant recipients.

The infectious dermatological disease or condition to be treated with the formulation as described herein, may be selected from the group consisting of bacterial infections, viral infections, fungal infections, parasitic infections, and combinations thereof.

The autoimmune dermatological disease or condition, or the cutaneous manifestation of the autoimmune condition to be treated with the formulation as described herein, may be selected from the group consisting of psoriasis, pemphigus, systemic lupus erythematodes, lichen planus, morphea, sclerodermia, epidermolysis bullosa, dermatomyositis, graft-versus-host syndrome.

The dermatological disease or condition to be treated with the formulation as described herein, may be selected from the group consisting of disorders of sweating, pigmentation disorders including hypopigmentation such as vitiligo, albinism and post inflammatory hypopigmentation and hyperpigmentation such as melasma, reactions to sunlight, such as sunburn, skin ageing, photosensitivity, disorders of hair follicles and sebaceous glands such as hypertrichosis, alopecia, male pattern baldness.

The pharmaceutical as described herein, in particular a pharmaceutical composition comprising a photosensitizer or a metabolic precursor thereof, preferably 5-aminolevulinic acid, a pharmaceutically acceptable salt, a derivative, precursor and/or metabolite thereof, as described herein, may be used in a method of photodynamic diagnosis of a neoplastic and/or proliferative dermatological disease or condition, such as benign or malignant neoplasia or precursors thereof; an inflammatory dermatological disease or condition; and/or a condition associated with bacterial proliferation such as acne.

The formulation as described herein, may be used in the treatment of a disease or condition, as described herein, for example neoplastic and/or proliferative dermatological diseases or conditions, such as benign or malignant skin neoplasia or precursors thereof, inflammatory dermatological diseases or conditions such as atopic dermatitis, eczema, psoriasis, rosacea or chronic wounds, and conditions associated with bacterial proliferation such as acne.

Yet another aspect of the present invention is a method for the preparation of the formulation as described herein, comprising the following steps:
(a) mixing the at least one lipophilic component, the at least one surfactant, and the at least one alcohol having at least three carbon atoms, and
(b) contacting the mixture obtained in step (a) with an aqueous component, under conditions allowing formation of a nanoemulsion, wherein the active agent is added under conditions allowing interactions of the active agent with the surface of the nanovesicles when dissolved in the aqueous phase.

In step (b), the conditions allowing formation of the nanoemulsion may include mixing both phases at an appropriate temperature and stirring in a fashion to form nanovesicle. The skilled person knows suitable temperature and stirring conditions. A vesicle size of less than or equal to 500 nm or less than or equal to 300 nm, preferably in the range of 5 nm to 200 nm, more preferably in the range of 5 nm to 100 nm can be obtained. In particular, the nanoemulsion of the present invention according to step (b) can be prepared without the use of high energy methods, which are well known in the art. High energy method includes high-pressure homogenization, microfluidization, and ultrasonication (Prev Nutr Food Sci. 2019 September; 24 (3): 225-234).

The method comprises a step of adding the active agent. Preferably, the active agent is a hydrophilic active pharmaceutical ingredient.

A hydrophilic compound, such as an amino acid, preferably a photosensitizer or a metabolic precursor, such as ALA, or/and a pharmaceutically acceptable salt thereof (such as ALA hydrochloride), can be added to the aqueous component before contacting the mixture obtained in step (a) with an aqueous component in step (b), such that the active agent may be non-covalently bound to the nanovesicles (in particular to the nanovesicle surface) in step (b).

A hydrophilic compound, such as an amino acid, preferably a photosensitizer or a metabolic precursor, such as ALA, or/and a pharmaceutically acceptable salt thereof (such as ALA hydrochloride), can also be added to the nanoemulsion obtained in step (b), such that the active agent may be non-covalently bound to the nanovesicles (in particular to the nanovesicle surface).

The method for the preparation the pharmaceutical formulation of the present invention can further comprise:
(i) adding a gelling agent, and/or
(ii) adding a preservative.

Yet another aspect of the present invention is a dispenser product or container product, comprising the formulation as described herein. In the dispenser product or container product, the formulation of the present invention is provided in a container or dispenser. Suitable dispensers and containers are known to the skilled person. For example, the dispenser may be a squeeze tube, comprising the formulation as described herein. The squeeze tube may contain the gel formulation as described herein. The dispenser may also be a metered dose dispenser or a foam dispenser.

The container or foam dispenser may comprise a propellant, wherein the propellant is provided to pressurize the container or foam dispenser. Any suitable propellant may be used. Suitable propellants and mixtures thereof are known to the skilled person. Preferably, the propellant is selected from propane, isobutane, n-butane and mixtures thereof.

The dispenser product may be a foam dispenser product, comprising a foam dispenser, as described herein. The foam dispenser comprises a container, wherein said container comprises the formulation as described herein, and a propellant. The propellant is provided to pressurize the foam dispenser. Any suitable propellant may be used, as described herein. A foam-generating device is mounted on the container. In particular, the formulation is prepared as a foamable formulation.

Yet another aspect of the present invention is the use of the formulation of the present invention, as described herein, for the manufacture of a medicament for the treatment and/or prevention of a dermatological disease or condition in a subject. In particular, the dermatological disease is a dermatological disease or condition as described herein.

Yet another aspect of the present invention is a method of treatment and/or prevention of a dermatological disease or condition in a subject, said method comprising administering to the subject, a pharmaceutically effective amount of the formulation as described herein. In particular, the dermatological disease is a dermatological disease or condition as described herein.

Yet another aspect of the present invention is a method of photodynamic diagnosis of a neoplastic and/or proliferative dermatological disease or condition, such as benign or malignant neoplasia or precursors thereof; an inflammatory dermatological disease or condition; and/or a condition associated with bacterial proliferation such as acne.

ALA (and derivatives) containing drugs drive the synthesis of fluorescent porphyrins that accumulate preferentially in cells/tissues with increased metabolic activity. This can be exploited in the method of photodynamic diagnostics, which can be applied to neoplastic diseases of the skin, such as benign or malignant neoplasia or precursors thereof, inflammatory conditions or conditions associated with bacterial proliferation such as acne. For photodynamic diagnosis, a ALA (or derivative) containing formulation is applied to the skin area to be diagnosed and incubated for an appropriate time (e.g., 1-3 h). Subsequently, blue spectrum light is applied to induce red fluorescence of accumulated porphyrins. The fluorescence can be detected by visual inspection or appropriate technical devices for qualitative or quantitative assessment.

The method of photodynamic diagnoses may comprise:
(i) administering the formulation comprising a photosensitizer or a metabolic precursor, such as 5-aminolevulinic acid, a pharmaceutically acceptable salt, a derivative, precursor and/or metabolite thereof, as described herein to the skin area to be diagnosed, under conditions allowing synthesis of fluorescent porphyrins in the cells and/or tissues, and
(ii) irradiating the skin area to which the formulation was administered, under conditions inducing fluorescence of accumulated porphyrins, wherein increased fluorescence of porphyrins indicates increased metabolic activity, being indicative for a neoplastic and/or proliferative dermatological disease or condition, an inflammatory dermatological disease or condition; and/or a condition associated with bacterial proliferation.

In step (i), the formulation may be incubated on the skin for e.g., 1-3 h.

in step (ii), the skin can be irradiated with light capable to induce red fluorescence of accumulated porphyrins. Suitable irradiation conditions are described herein.

Diagnosis of the neoplastic and/or proliferative dermatological disease or condition, can be performed by detection of increased fluorescence (e.g., compared with healthy tissue and/or skin, e.g., adjacent to the suspected area). Detection of fluorescence can be performed by visual inspection or appropriate technical devices for qualitative or quantitative assessment.

Diagnosis according to the method described herein may be performed for demarcation of tumor borders to assist surgery, to assess treatment efficacy, and/or the assessment of light induced photobleaching for light dosimetry in photodynamic therapy.

An alternative aspect of the invention relates to a formulation as described in the first aspect of the invention, but comprising propylene glycol. The formulation of the alternative aspect may be free of, may be essentially free of, or may comprise less than an indicated amount, such as less than 1%, less than or equal to 0.99%, less than or equal to 0.95%, less than or equal to 0.9%, less than or equal to 0.8%, less than or equal to 0.7%, less than or equal to 0.6%, less than or equal to 0.5%, less than or equal to 0.4%, less than or equal to 0.3%, less than or equal to 0.2% or less than or equal to 0.1% of one polyol, all polyols or any chosen number of polyols selected from the group consisting of glycerin, diglycerin, polyglycerin, diethylene glycol, dipropylene glycol, butylene glycol, pentylene glycol, hexylene glycol, 1,3-propanediol, 1,5-pentanediol, octane-1,2-diol, polyethyleneglycols, particularly having from 2 to 50 ethylene oxide groups, and monosaccharides or disaccharides such as sorbitol, mannitol and mixtures thereof. The formulation of the alternative aspect may be essentially free of one polyol or any chosen number of polyols selected from the group consisting of glycerin, diglycerin, polyglycerin, diethylene glycol, dipropylene glycol, butylene glycol, pentylene glycol, hexylene glycol, 1,3-propanediol, 1,5-pentanediol, octane-1,2-diol, polyethyleneglycols, particularly having from 2 to 50 ethylene oxide groups, and monosaccharides or disaccharides such as sorbitol, mannitol and mixtures thereof.

The invention also pertains to the following embodiments:
1. A formulation comprising
   (a) a nanoemulsion comprising:
      (i) at least one aqueous component;
      (ii) a carrier component comprising:
         (1) at least one lipophilic component,
         (2) at least one surfactant, and
         (3) at least one alcohol; and
   (b) an active agent comprising a carboxylic acid group, or a derivative, or salt of a carboxylic acid group,
   wherein the formulation comprises less than 1% w/w of propylene glycol or no propylene glycol.
2. The formulation of embodiment 1, wherein the formulation comprises less than or equal to 0.9% w/w of propylene glycol or no propylene glycol.
3. The formulation of embodiment 1 or 2, preferably 2, wherein the formulation comprises essentially no propylene glycol.

4. The formulation of any one of embodiments 1 to 3, preferably 3, wherein the formulation comprises no propylene glycol.
5. The formulation of any one of embodiments 1 to 4, preferably 4, wherein the formulation comprises no, essentially no, less than 1%, or less than or equal to 0.99%, 0.95%, 0.9%, 0.8%, 0.7%, 0.6%, 0.5%, 0.4%, 0.3%, 0.2%, or 0.1% w/w of a non-cyclic polyol having 2 to 5 carbon atoms.
6. The formulation of any one of embodiments 1 to 5, preferably 5, wherein the formulation comprises no, essentially no, less than 1%, or less than or equal to 0.99%, 0.95%, 0.9%, 0.8%, 0.7%, 0.6%, 0.5%, 0.4%, 0.3%, 0.2%, or 0.1% w/w of a polyol having 2 to 12 carbon atoms.
7. The formulation of any one of embodiments 1 to 6, wherein
the at least one alcohol comprises at least three carbon atoms, preferably 3, 4 or 5 carbon atoms, more preferably the at least one alcohol is selected from the group consisting of 1-propanol and 2-propanol and mixtures thereof;
the at least one lipophilic component is selected from triglycerides and mixtures thereof, preferably wherein the at least one lipophilic component is a caprylic and/or a capric triglyceride or a mixture thereof; and/or
the at least one surfactant is selected from the group consisting of a phospholipid, a lysophospholipid, a ceramide and/or a mixture thereof, and/or the at least one surfactant is a polyoxyethylene-type surfactant.
8. The formulation of any one of embodiments 1 to 7, comprising a total aqueous component in an amount of 50% to 99% (w/w), preferably from 70% to 95% (w/w), more preferably from 75% to 95% (w/w), even more preferably from 80% to 90% (w/w).
9. The formulation of any one of embodiments 1 to 8, comprising
(a) the at least one lipophilic component in an amount from 0.1% to 30% (w/w), preferably from 0.25% to 15% (w/w), preferably from 0.25% to 10% (w/w), and more preferably from 2% to 10% (w/w) or 3% to 8% (w/w); and/or
(b) the at least one alcohol in an amount from 0.1% to 10% (w/w), preferably from 0.5% to 5% (w/w), more preferably from 1% to 5% (w/w) and even more preferably from 1% to 3%,
based on the total weight of the nanoemulsion (a).
10. The formulation of any one of embodiments 1 to 9, wherein the active agent is a photosensitizer or a metabolic precursor thereof.
11. The formulation of any one of embodiments 1 to 10, wherein the active agent is 5-aminolevulinic acid, a derivative, a precursor, a metabolite, and/or a pharmaceutically acceptable salt thereof.
12. The formulation of any one of embodiments 1 to 11, wherein the active agent is present in an amount of from 0.1% to 25% (w/w), based on the total weight of the formulation.
13. The formulation of any one of embodiments 1 to 12, wherein the nanoemulsion comprises nanovesicles, wherein the nanovesicles have a size of less than or equal to 500 nm, preferably less than or equal to 200 nm, more preferably in the range of 5 nm to 200 nm when
a) stored for one month, two months, three months, six months, twelve months or at least one month, at least two months, at least three months, at least six months or at least twelve months at 2-25° C.; and/or
b) stored for one month, two months, three months, six months, twelve months, eighteen months, twenty-four months, thirty months, thirty-six months or at least one month, at least two months, at least three months, at least six months or at least twelve months, at least eighteen months, at least twenty-four months, at least thirty months or at least thirty-six months at 2-8° C.
14. The formulation of any one of embodiments 1 to 13, characterized by a polydispersity index of less than or equal to 0.4 when
a) stored for one month, two months, three months, six months, twelve months or at least one month, at least two months, at least three months, at least six months or at least twelve months at 2-25° C.; and/or
b) stored for one month, two months, three months, six months, twelve months, eighteen months, twenty-four months, thirty months, thirty-six months or at least one month, at least two months, at least three months, at least six months or at least twelve months, at least eighteen months, at least twenty-four months, at least thirty months or at least thirty-six months at 2-8° C.
15. The formulation of any one of embodiments 1 to 14, comprising at least one gelling agent, preferably wherein the gelling agent is selected from the group consisting of poloxamer, xanthan, bentonite, sodium carboxymethylcellulose, hydroxymethyl cellulose, carbomer, hydroxypropyl cellulose, gellan gum, guar gum, pectin, poly(ethylene)oxide, polycarbophil, alginate, tragacanth, povidone, gelatin, and mixtures thereof, more preferably wherein the gelling agent is selected from poloxamer, xanthan and mixtures thereof.
16. The formulation of any one of embodiments 1 to 15, which is essentially free of parabens.
17. A formulation comprising
(a) a nanoemulsion comprising:
(i) at least one aqueous component;
(ii) a carrier component comprising:
(4) at least one lipophilic component,
(5) at least one surfactant, and
(6) at least one alcohol; and
(b) an active agent comprising a carboxylic acid group, or a derivative, or salt of a carboxylic acid group, wherein the active agent is a photosensitizer or a metabolic precursor thereof;
wherein the formulation comprises essentially no propylene glycol.
18. The formulation of embodiment 17, wherein the active agent is 5-aminolevulinic acid, a derivative, a precursor, a metabolite, and/or a pharmaceutically acceptable salt thereof.
19. A formulation comprising
(a) a nanoemulsion comprising:
(i) at least one aqueous component;
(ii) a carrier component comprising:
(7) at least one lipophilic component,
(8) at least one surfactant, and
(9) at least one alcohol; and
(b) 5-aminolevulinic acid, a derivative, a precursor, a metabolite, and/or a pharmaceutically acceptable salt thereof,
wherein the formulation comprises less than 1% w/w of propylene glycol or no propylene glycol.

20. A method of treating a dermatological disease or condition, comprising administration of an effective amount of the formulation of embodiment 10 to 12 to a subject in need thereof.

The invention also pertains to the following items:
1. A formulation comprising
   (a) a nanoemulsion, said emulsion comprising:
      (i) at least one aqueous component;
      (ii) a carrier component comprising:
         (1) at least one lipophilic component,
         (2) at least one surfactant, and
         (3) at least one alcohol; and
   (b) an active agent comprising a carboxylic acid group or a derivative, or salt of a carboxylic acid group, wherein the formulation comprises less than 1% w/w of propylene glycol, preferably less than or equal to 0.99%, 0.95% or 0.9% w/w of propylene glycol or no propylene glycol.
2. The formulation of item 1, wherein the formulation comprises essentially no propylene glycol.
3. The formulation of any of the preceding items, wherein the formulation comprises no, essentially no, less than 1%, or less than or equal to 0.99%, 0.95%, 0.9%, 0.8%, 0.7%, 0.6%, 0.5%, 0.4%, 0.3%, 0.2%, or 0.1% w/w of a non-cyclic polyol having 2 to 3 carbon atoms, preferably no, essentially no, less than 1%, or less than or equal to 0.99%, 0.95%, 0.9%, 0.8%, 0.7%, 0.6%, 0.5%, 0.4%, 0.3%, 0.2%, or 0.1% w/w of a non-cyclic polyol having 2 to 5 carbon atoms.
4. The formulation of any of the preceding items, wherein the formulation comprises no, essentially no, less than 1%, or less than or equal to 0.99%, 0.95%, 0.9%, 0.8%, 0.7%, 0.6%, 0.5%, 0.4%, 0.3%, 0.2%, or 0.1% w/w of a polyol having 2 to 5 carbon atoms, preferably no, essentially no, less than 1%, or less than or equal to 0.99%, 0.95%, 0.9%, 0.8%, 0.7%, 0.6%, 0.5%, 0.4%, 0.3%, 0.2%, or 0.1% w/w of a polyol having 2 to 12 carbon atoms.
5. The formulation of any of the preceding items, wherein the at least one alcohol comprises at least three carbon atoms, preferably 3, 4 or 5 carbon atoms.
6. The formulation of any of the preceding items, wherein the active agent is a photosensitizer or a metabolic precursor thereof.
7. The formulation of any of the preceding items, wherein the active agent is present in an amount of from 0.01% to 25% (w/w), preferably 0.1% to 25% (w/w), more preferably 1% to 25% (w/w), based on the total weight of the formulation.
8. The formulation of any of the preceding items, wherein the active agent is 5-aminolevulinic acid, a derivative, a precursor, a metabolite, and/or a pharmaceutically acceptable salt thereof.
9. The formulation of item 8, wherein the 5-aminolevulinic acid, the derivative, the precursor, the metabolite thereof, and/or the pharmaceutically acceptable salt thereof, is present in an amount of from 0.01% to 25% (w/w), preferably 0.1% to 25% (w/w), more preferably 1% to 25% (w/w), based on the total weight of the formulation.
10. The formulation of any one of the items 8 or 9, wherein the formulation comprises an entity characterized by m/z=246 in an amount of less than or equal to 1.5%, 1.0% or 0.75% when stored for 3 months at 40° C.
11. The formulation of any one of the items 8 to 10, wherein the formulation comprises an entity characterized by m/z=246 in an amount of less than or equal to 1.5%, 1.0%, 0.5% or 0.2% when stored for 6 months at 25° C.
12. The formulation of any of the preceding items, wherein the formulation is a pharmaceutical formulation.
13. The formulation of any of the preceding items, wherein the formulation is for topical use and/or wherein the formulation is a lotion, a spray, a foam, an emulsion, a nanoemulsion, a gel or a cream.
14. The formulation of any of the preceding items, wherein the active agent is dissolved in the aqueous phase and/or is capable to interact with the surface of the nanovesicles.
15. The formulation of any of the preceding items, wherein the active agent is a hydrophilic active agent
16. The formulation of any one of the preceding items, wherein the nanoemulsion comprises nanovesicles, wherein the nanovesicles have a size of less than or equal to 500 nm, preferably in the range of 5 nm to 200 nm when stored for one month at 40° C.
17. The formulation of any one of the preceding items, wherein the nanoemulsion comprises nanovesicles, wherein the nanovesicles have a size of less than or equal to 500 nm, preferably in the range of 5 nm to 200 nm when stored for six months at 25° C.
18. The formulation of any one of the preceding items, wherein the aqueous component is present in an amount of 50% to 99% w/w, based on the total weight of the nanoemulsion (a), preferably from 70% to 95% (w/w), and more preferably from 80% to 95% (w/w).
19. The formulation of any one of the preceding items, wherein the aqueous component comprises at least one pH buffering agent.
20. The formulation of item 19, wherein the pH buffering agent is selected from the group consisting of citrate, phosphate, acetate and carbonate.
21. The formulation of any one of the preceding items, having a pH of 2-6.
22. The formulation of any one of the preceding items, having a pH of 2-4.
23. The formulation of any one of the preceding items, wherein the at least one lipophilic component is selected from triglycerides and mixtures thereof.
24. The formulation of any one of the preceding items, wherein the at least one lipophilic component comprises a caprylic and/or a capric triglyceride or a mixture thereof.
25. The formulation of any one of the preceding items, wherein the at least one lipophilic component is present in an amount of from 0.1% to 30% (w/w), based on the total weight of the nanoemulsion (a), preferably from 0.25% to 10% (w/w), and more preferably from 0.5% to 8% (w/w) or 3% to 8% (w/w).
26. The formulation of any one of the preceding items, wherein the at least one surfactant comprises (a) a phospholipid, a lysophospholipid, a ceramide and/or a mixture thereof, and/or (b) a polyoxyethylene-type surfactant.
27. The formulation of any one of the preceding items, wherein the at least one surfactant comprises lecithin, preferably soy lecithin.
28. The nanoemulsion of item 27, wherein the lecithin has a phosphatidylcholine content of at least 80% by weight.
29. The formulation of any one of items 26-28, wherein the phospholipid, the lysophospholipid, the ceramide and/or the mixture thereof is present in an amount of from 0.1% to 10% (w/w), based on the total weight of nanoemulsion (a), preferably from 0.15% to 5% (w/w), and more preferably from 0.2% to 3% (w/w).

30. The formulation of any one of the items 26-29, wherein the polyoxyethylene-type surfactant comprises Polysorbate 80.

31. The formulation of any one of items 26-30, wherein the polyoxyethylene-type surfactant is present in an amount of from 0.1% to 10% (w/w), based on the total weight of the nanoemulsion (a), more preferably from 0.2% to 5% (w/w), and most preferably from 0.5% to 5% (w/w).

32. The formulation of any one of the preceding items, wherein at least one alcohol is selected from the group consisting of 1-propanol or 2-propanol and a mixture thereof.

33. The formulation of any one of the preceding items, wherein the at least one alcohol is present in an amount of from 0.1% to 10% (w/w), based on the total weight of the nanoemulsion (a), preferably from 0.5% to 5% (w/w), and more preferably from 1% to 2% (w/w).

34. The formulation of any one of the preceding items, comprising at least one gelling agent.

35. The formulation of any one of the preceding items, wherein the gelling agent is selected from the group consisting of poloxamer, xanthan gum, bentonite, sodium carboxymethylcellulose, hydroxymethyl cellulose, carbomer, hydroxypropyl cellulose, gellan gum, guar gum, pectin, poly(ethylene)oxide, polycarbophil, alginate, tragacanth, povidone, gelatin, and mixtures thereof.

36. The formulation of item 34 or 35, wherein the gelling agent is selected from poloxamer, xanthan and/or mixtures thereof.

37. The formulation of any one of the preceding items, wherein the gelling agent is present in an amount of from 0.1% to 10% (w/w), based on the total weight of the formulation, preferably from 0.25% to 5% (w/w), and more preferably from 1% to 4% (w/w).

38. The formulation of any one of the preceding items, further comprising at least one preservative.

39. The formulation of item 38, wherein the preservative is benzoate, preferably sodium benzoate.

40. The formulation of item 38 or 39, wherein the preservative is present in an amount of from 0.01% to 3% w/w, based on the total weight of the formulation, preferably from 0.2% to 2% (w/w), and more preferably from 0.2% to 1.5% (w/w).

41. The formulation of any one of the preceding items, which is essentially free of parabens.

42. The formulation of any one of the preceding items, characterized by a polydispersity index of less than or equal to 0.8, wherein the polydispersity index is determined by dynamic light scattering.

43. The formulation of any one of the items 1-42, comprising:
   (a) an emulsion of nanovesicles comprising
      (i) an aqueous component, present in an amount of 70% to 95% w/w, based on the total weight of the nanoemulsion (a).
      (ii) nanovesicles, comprising
         (1) 1-5% of at least one phospholipid, based on the total weight of the nanoemulsion (a);
         (2) 2-10% of at least one polyoxyethylene-type surfactant, based on the total weight of the nanoemulsion (a);
         (3) 1-5% $C_3$ to $C_5$ alcohol, based on the total weight of the nanoemulsion (a); and
         (4) 2-10% triglycerides, based on the total weight of the nanoemulsion (a);
   (b) 0.1-20% of a photosensitizer or a metabolic precursor thereof, preferably 5-aminolevulinic acid hydrochloride, based on the total weight of the formulation;
   (c) 0.1-2% of at least one preservative, based on the total weight of the formulation; and wherein the formulation essentially does not comprise propylene glycol, and wherein the formulation preferably has a pH of 2-4.

44. The formulation of any one of the preceding items, provided in a container, wherein the container further comprises a propellant, and wherein the propellant is provided to pressurize the container and/or to pressurize the formulation in the container.

45. The formulation of any one of the preceding items, for use in medicine.

46. The formulation of any one of the preceding items, for use in a method of treatment and/or prevention of a dermatological disease or condition in a subject.

47. The formulation of any one of the preceding items, for use in a method of treatment and/or prevention of a dermatological disease or condition in a subject, wherein the treatment and/or prevention of the dermatological disease or condition comprises:
   (a) topically administering to the subject, a pharmaceutically effective amount of the formulation of any one of the items 1-46, to a diseased or affected area and optionally an area surrounding the diseased or affected area of the skin, and
   (b) incubating the pharmaceutically formulation on the skin of the subject with or without occlusion of the area of the skin to which the formulation was administered, the occlusion preferably performed using low density polyethylene or polyurethane film, to enhance deep layer tissue penetration.

48. The formulation for use of item 47, further comprising the step:
   (c) irradiating the skin area to which the formulation was administered, with light.

49. The formulation for use of any one of the items 47-48, wherein the area surrounding the diseased or affected area of the skin includes an area of at least about 5 mm width.

50. The formulation for use of any one of the items 46-49, wherein the dermatological disease or condition includes diseases or conditions of the skin, skin appendages or mucosa.

51. The formulation for use of any one of the items 46-50, wherein the dermatological disease or condition is selected from the group consisting of inflammatory, neoplastic, proliferative, infectious, and/or autoimmune diseases or conditions, and/or the cutaneous manifestation thereof, and/or diseases associated with single lesions or fields of lesions, neoplastic, proliferative and/or inflammatory changes.

52. The formulation for use of item 51, wherein the inflammatory dermatological disease or condition is selected from the group consisting of dermatitis, contact dermatitis, acne, atopic dermatitis, eczema, pustular dermatitis, seborrheic dermatitis, perioral dermatitis, chronic wound, urticaria, skin ulcer, rosacea, rash, drug eruptions, toxic epidermal necrolysis;

erythema multiforme, erythema nodosum, granuloma annulare, and other cutaneous manifestations of inflammation.
53. The formulation for use of item 51, wherein the neoplastic and/or proliferative dermatological disease or condition is selected from the group consisting of basal cell carcinoma, preferably superficial basal cell carcinoma or nodular basal cell carcinoma; squamous cell carcinoma, preferably Morbus Bowen or invasive squamous cell carcinoma; vulvar intraepithelial neoplasia (VIN); cutaneous T-cell lymphoma; Merkel cell carcinoma; hemangioma; a nodular or subcutaneous cancer disease; field cancerization; non-melanoma skin cancer in organ transplant recipients; and prevention of non-melanoma skin cancer in organ transplant recipients.
54. The formulation for use of item 51, wherein the infectious dermatological disease or condition is selected from the group consisting of bacterial infections, viral infections, fungal infections, parasitic infections, and combinations thereof.
55. The formulation for use of item 51, wherein the autoimmune dermatological disease or condition, or the cutaneous manifestation of the autoimmune condition is selected from the group consisting of psoriasis, pemphigus, systemic lupus erythematodes, lichen planus, morphea, sclerodermia, epidermolysis bullosa, dermatomyositis, graft-versus-host syndrome.
56. The formulation for use of any one of the items 47-50, wherein the dermatological disease or condition is selected from the group consisting of disorders of sweating, pigmentation disorders including hypopigmentation such as vitiligo, albinism and post inflammatory hypopigmentation and hyperpigmentation such as melasma, reactions to sunlight, such as sunburn, skin ageing, photosensitivity, disorders of hair follicles and sebaceous glands such as hypertrichosis, alopecia, male pattern baldness.
57. The formulation of any one of the preceding items, for use in a method of photodynamic diagnosis of a neoplastic and/or proliferative dermatological disease or condition, such as benign or malignant neoplasia or precursors thereof; an inflammatory dermatological disease or condition; and/or a condition associated with bacterial proliferation such as acne.
58. A method for the preparation the formulation of any one of the items 1-57, comprising the following steps:
    (a) mixing the at least one lipophilic component, the at least one surfactant, and the at least one alcohol having at least three carbon atoms, and
    (b) contacting the mixture obtained in step (a) with an aqueous component, under conditions allowing formation of a nanoemulsion, wherein the active agent is added under conditions allowing interactions of the active agent with the surface of the nanovesicles when dissolved in the aqueous phase.
59. The method of item 58, further comprising
    (i) adding a gelling agent, and/or
    (ii) adding a preservative.
60. A dispenser product, comprising the formulation of any one of the items 1-57.
61. A container, comprising the formulation of any one of the items 1-57.
62. Use of the formulation according to any one of the items 1-57, for the manufacture of a medicament for the treatment and/or prevention of a dermatological disease or condition in a subject.
63. A method of treatment and/or prevention of a dermatological disease or condition in a subject, said method comprising administering to the subject, a pharmaceutically effective amount of the formulation of any one of the items 1 to 57.
64. A method of photodynamic diagnosis of a neoplastic and/or proliferative dermatological disease or condition, such as benign or malignant neoplasia or precursors thereof; an inflammatory dermatological disease or condition; and/or a condition associated with bacterial proliferation such as acne, said method comprising
    (i) administering the formulation according to any one of the items 1-57 to the skin area to be diagnosed, under conditions allowing synthesis of fluorescent porphyrins in the cells and/or tissues, and
    (ii) irradiating the skin area to which the formulation was administered, under conditions inducing fluorescence of accumulated porphyrins,
    wherein increased fluorescence of porphyrins indicates increased metabolic activity, being indicative for a neoplastic and/or proliferative dermatological disease or condition, an inflammatory dermatological disease or condition; and/or a condition associated with bacterial proliferation.

The invention also pertains to the following items:
1. A formulation comprising
    (a) a nanoemulsion comprising:
        (i) at least one aqueous component;
        (ii) a carrier component comprising:
            (1) at least one lipophilic component,
            (2) at least one surfactant, and
            (3) at least one alcohol; and
    (b) an active agent comprising a carboxylic acid group, or a derivative, or salt of a carboxylic acid group,
    wherein the formulation comprises less than 1% w/w of propylene glycol or no propylene glycol.
2. The formulation of item 1, wherein the formulation comprises less than or equal to 0.9% w/w of propylene glycol or no propylene glycol.
3. The formulation of any one of the preceding items, wherein the formulation comprises essentially no propylene glycol.
4. The formulation of any one of the preceding items, wherein the formulation comprises no propylene glycol.
5. The formulation of any of the preceding items, wherein the formulation comprises no, essentially no, less than 1%, or less than or equal to 0.99%, 0.95%, 0.9%, 0.8%, 0.7%, 0.6%, 0.5%, 0.4%, 0.3%, 0.2%, or 0.1% w/w of a non-cyclic polyol having 2 to 5 carbon atoms.
6. The formulation of any one of the preceding items, wherein the formulation comprises no, essentially no, less than 1%, or less than or equal to 0.99%, 0.95%, 0.9%, 0.8%, 0.7%, 0.6%, 0.5%, 0.4%, 0.3%, 0.2%, or 0.1% w/w of a polyol having 2 to 12 carbon atoms.
7. The formulation of any one of the preceding items, wherein the at least one alcohol comprises at least three carbon atoms, preferably 3, 4 or 5 carbon atoms, more preferably the at least one alcohol is selected from the group consisting of 1-propanol and 2-propanol and mixtures thereof.
8. The formulation of any one of the preceding items, wherein the at least one lipophilic component is selected from triglycerides and mixtures thereof, preferably wherein the at least one lipophilic component is a caprylic and/or a capric triglyceride or a mixture thereof.

9. The formulation of any one of the preceding items, wherein the at least one surfactant is selected from the group consisting of a phospholipid, a lysophospholipid, a ceramide and/or a mixture thereof, and/or the at least one surfactant is a polyoxyethylene-type surfactant.

10. The formulation of any one of the preceding items, comprising a total aqueous component in an amount of 50% to 99% (w/w), preferably from 70% to 95% (w/w), more preferably from 75% to 95% (w/w), even more preferably from 80% to 90% (w/w).

11. The formulation of any one of the preceding items, comprising
    (a) the at least one lipophilic component in an amount from 0.1% to 30% (w/w), preferably from 0.25% to 15% (w/w), preferably from 0.25% to 10% (w/w), and more preferably from 2% to 10% (w/w) or 3% to 8% (w/w); and/or
    (b) the at least one alcohol in an amount from 0.1% to 10% (w/w), preferably from 0.5% to 5% (w/w), more preferably from 1% to 5% (w/w) and even more preferably from 1% to 3%,
    based on the total weight of the nanoemulsion (a).

12. The formulation of any one of the preceding items, wherein the active agent is a hydrophilic active agent.

13. The formulation of any one of the preceding items, wherein the active agent is a photosensitizer or a metabolic precursor thereof.

14. The formulation of any one of the preceding items, wherein the active agent is 5-aminolevulinic acid, a derivative, a precursor, a metabolite, and/or a pharmaceutically acceptable salt thereof.

15. The formulation of any one of the preceding items, wherein the active agent is present in an amount of from 0.1% to 25% (w/w), based on the total weight of the formulation.

16. The formulation of any one of the preceding items, wherein the nanoemulsion comprises nanovesicles, wherein the nanovesicles have a size of less than or equal to 500 nm, preferably less than or equal to 200 nm, more preferably in the range of 5 nm to 200 nm when
    a) stored for one month, two months, three months, six months, twelve months or at least one month, at least two months, at least three months, at least six months or at least twelve months at 2-25° C.; and/or
    b) stored for one month, two months, three months, six months, twelve months, eighteen months, twenty-four months, thirty months, thirty-six months or at least one month, at least two months, at least three months, at least six months or at least twelve months, at least eighteen months, at least twenty-four months, at least thirty months or at least thirty-six months at 2-8° C.

17. The formulation of any one of the preceding items, characterized by a polydispersity index of less than or equal to 0.4 when
    a) stored for one month, two months, three months, six months, twelve months or at least one month, at least two months, at least three months, at least six months or at least twelve months at 2-25° C.; and/or
    b) stored for one month, two months, three months, six months, twelve months, eighteen months, twenty-four months, thirty months, thirty-six months or at least one month, at least two months, at least three months, at least six months or at least twelve months, at least eighteen months, at least twenty-four months, at least thirty months or at least thirty-six months at 2-8° C.

18. The formulation of any one of the preceding items, comprising at least one gelling agent, preferably wherein the gelling agent is selected from the group consisting of poloxamer, xanthan, bentonite, sodium carboxymethylcellulose, hydroxymethyl cellulose, carbomer, hydroxypropyl cellulose, gellan gum, guar gum, pectin, poly(ethylene)oxide, polycarbophil, alginate, tragacanth, povidone, gelatin, and mixtures thereof, more preferably wherein the gelling agent is selected from poloxamer, xanthan and mixtures thereof.

19. The formulation of any one of the preceding items, which is essentially free of parabens.

20. The formulation of any one of the preceding items, for use in medicine, in particular for use in a method of treatment and/or prevention of a dermatological disease or condition.

The present invention is further illustrated by the following figures and Examples.

FIGURE LEGENDS

FIG. 1: Content of known impurity (2-hydroxypropyl-δ-aminolevulinate, m/z 190) and m/z 246-impurity in Formulation 1 (with propylene glycol) and Formulation 2 (without propylene glycol) after storage for 6 months at 25° C. or 40° C.

Figure 2:
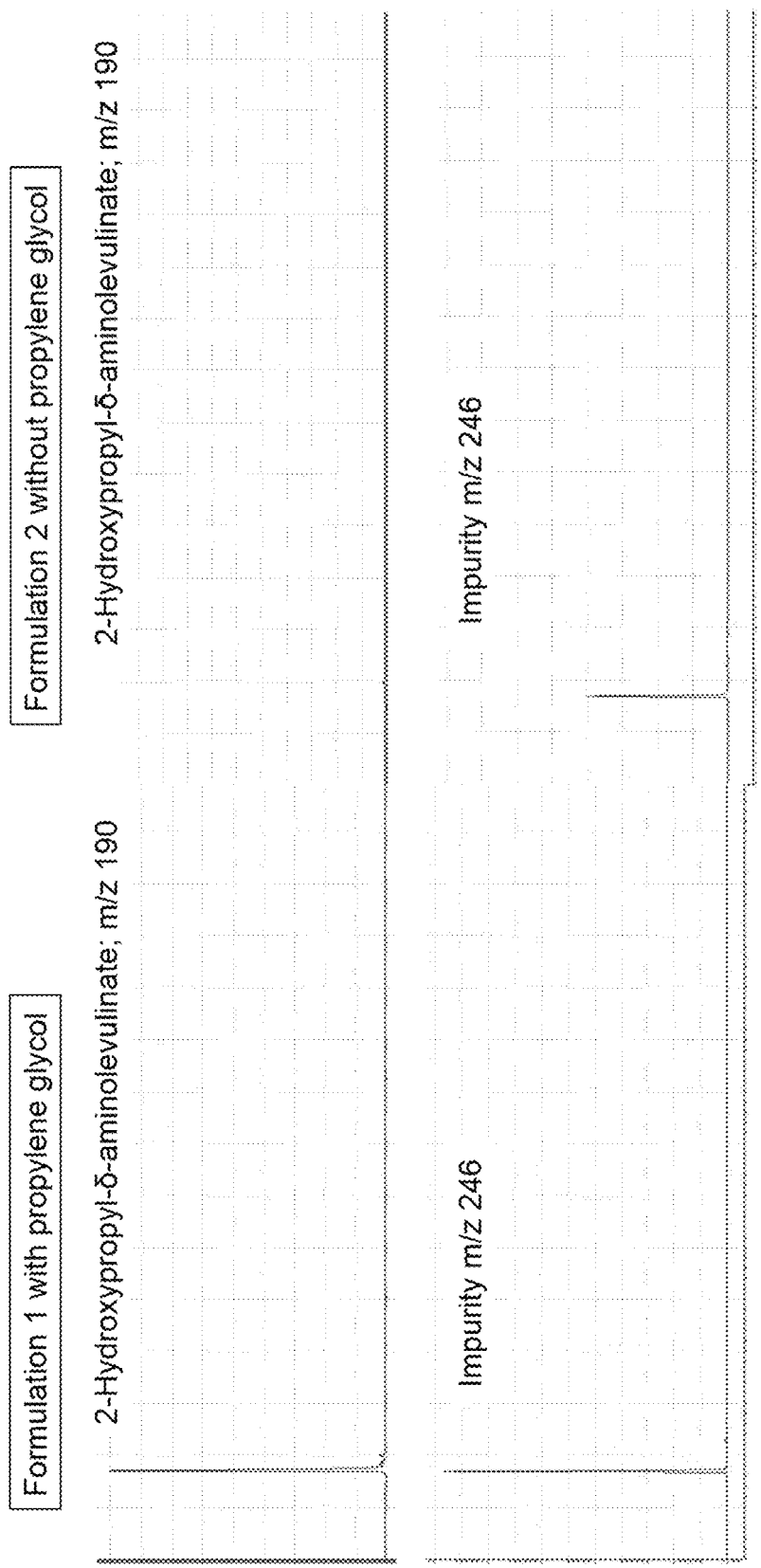

FIG. 2: Chromatograms of known impurity (2-hydroxypropyl-δ-aminolevulinate; m/z 190) and m/z 246-impurity in Formulation 1 (with propylene glycol) and Formulation 2 (without propylene glycol) after storage for 3 months at 40° C.

Figure 3:
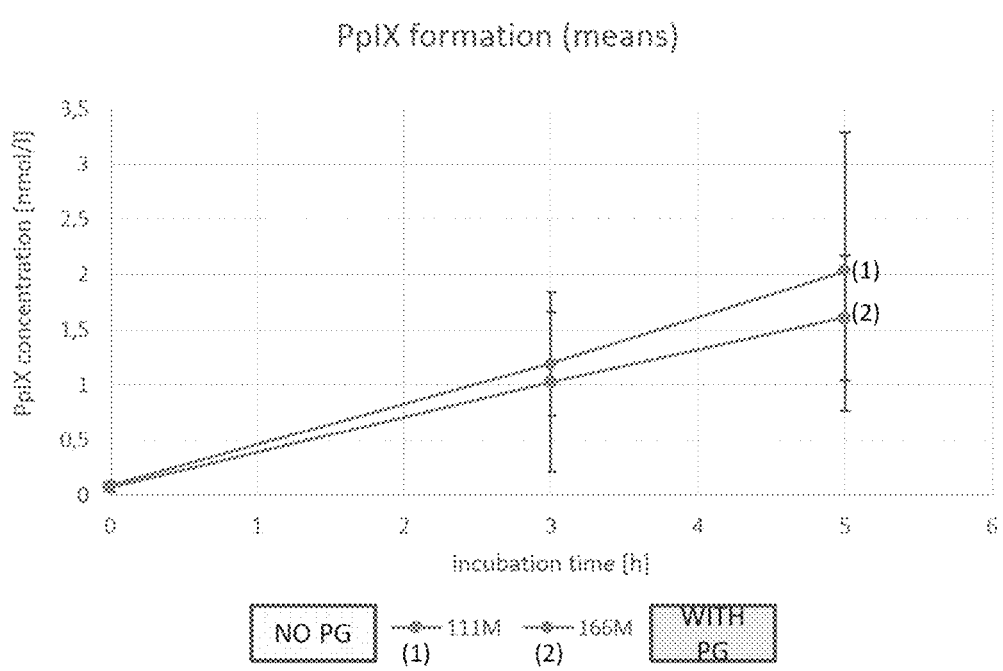

FIG. 3: Skin penetration of Formulation 1 (with propylene glycol) and Formulation 2 (without propylene glycol) in ex vivo human skin. PpIX: protoporphyrin IX. Error bars indicate standard deviation.

Figure 4:
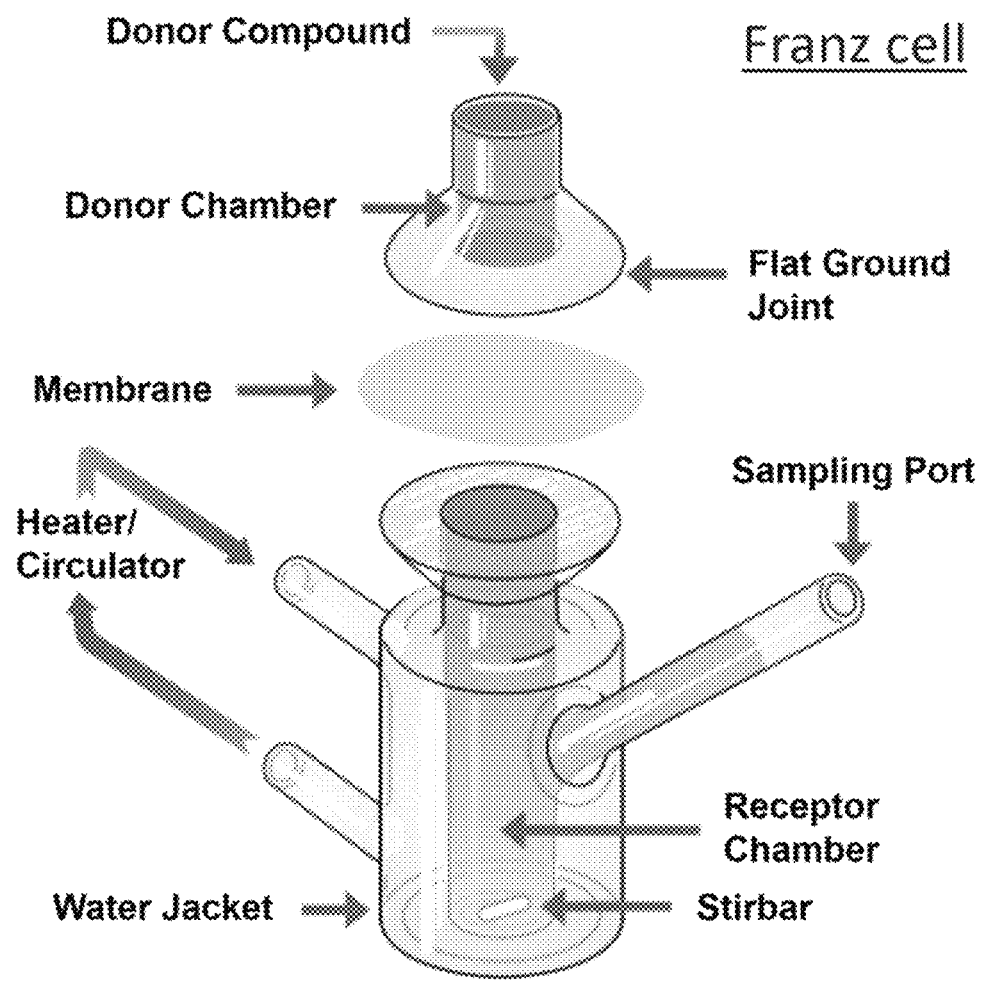
Figure 4:
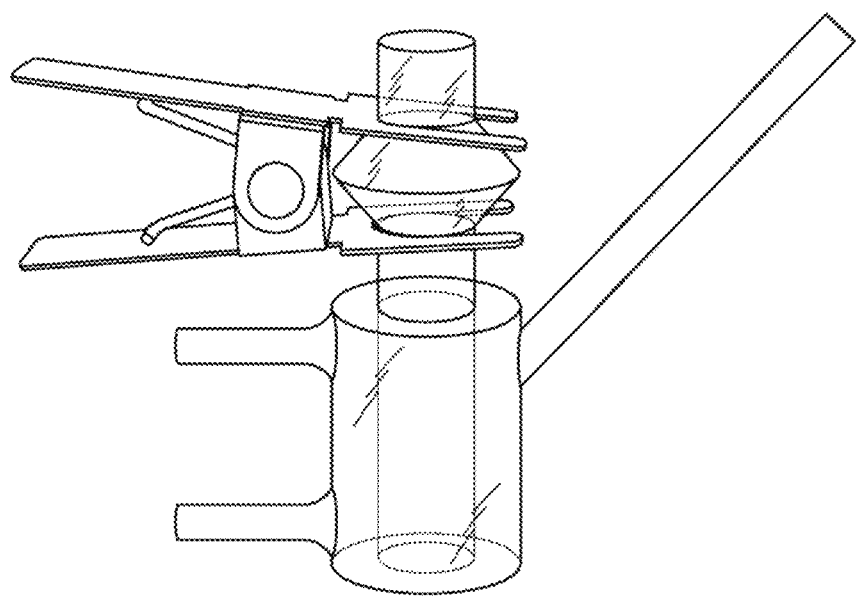

FIG. 4: Franz cell (top: scheme, bottom: photograph)

Figure 5:
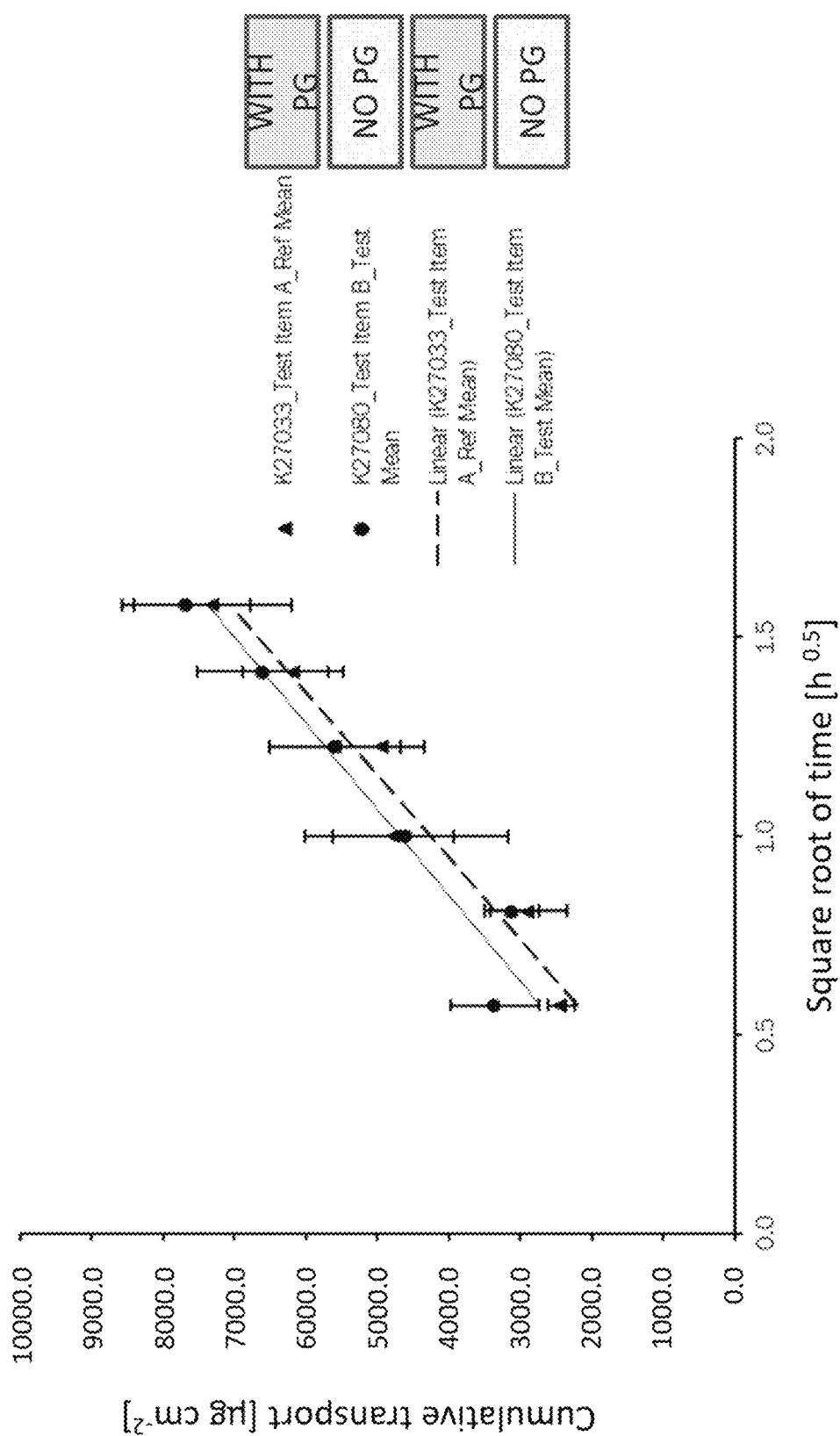

FIG. 5: Release of 5-ALA from Formulation 1 (with propylene glycol) and Formulation 2 (without propylene glycol) after 2.5 hours (linear range of Higuchi plot). The values shown are the mean values from the experiment six-fold. The cumulative transport into the acceptor compartment is expresses as μg per cm² of membrane area against square root of time.

EXAMPLES

Example 1: Preparation of Nanoemulsions BF200, BF215 and BF220

TABLE 1

| Lipophilic content of nanoemulsions used in the Examples |  |
| --- | --- |
| BF200 | 10% lipophilic content |
| BF215 | 15% lipophilic content |
| BF220 | 20% lipophilic content |

The qualitative and quantitative compositions of the nanoemulsions BF200, BF215 and BF220 are given in Table 2.

TABLE 2

Composition of nanoemulsions BF200, BF215 and BF220

| | Ingredient | Content (% w/w) BF200 | Content (% w/w) BF215 | Content (% w/w) BF220 | Function | Quality |
|---|---|---|---|---|---|---|
| 1 | Soy lecithin | 1.7 | 2.0-3.0 | 3.0-4.0 | surfactant | >90% phosphadidylcholine, for pharmaceutical use, USP |
| 2 | Polysorbate 80 (polyoxyethylene sorbitol monooleate) | 3.4 | 4.5-5.5 | 6.0-7.0 | surfactant | Ph. Eur. |
| 3 | Caprylic/capric triglycerides | 3.5 | 4.5-5.5 | 6.0-8.0 | lipid core | Ph. Eur. |
| 4 | Isopropyl alcohol | 1.4 | 2.0-3.0 | 2.0-4.0 | solvent | Ph. Eur. |
| | Content (% w/w) ingredients 1-4 | 10.0 | 15.0 | 20.0 | | |
| | 10 mM phosphate buffer, pH 6 | ad 100.00 | ad 100.00 | ad 100.00 | solvent | Water for injection: Ph. Eur.; Disodium phosphate and sodium hydrogen phosphate: Ph. Eur. |

The manufacturing process for the nanoemulsions in a typical batch size consists of the following steps 1-4:

Step 1: Preparation of a 10 mM Phosphate Buffer (Aqueous Component)

10 mM phosphate buffer (1000 g), pH 6, was prepared and the phosphate buffer optionally sterilized by filtration through a sterile filter.

Step 2: Preparation of a Carrier Containing the Lipophilic Component, the Surfactants and the Alcohol

TABLE 3

Carrier component

| Ingredient | Weight (g) |
|---|---|
| Soy lecithin | 17 |
| Polysorbate 80 (polyoxyethylene sorbitol monooleate) | 34 |
| Caprylic/capric triglycerides | 35 |
| Isopropyl alcohol | 14 |

Soy lecithin (17 g) was weighed in a suitable vessel, isopropyl alcohol (14 g) was added and the vessel was covered to avoid alcohol evaporation. Soy lecithin was dissolved under continuous stirring with a suitable stirrer at room temperature. Caprylic/capric triglycerides (35 g) and Polysorbate 80 (34 g) were weighed and added to the solution of soy lecithin. The mixture was stirred with a suitable stirrer at room temperature until a homogenous clear solution was obtained.

This solution is the carrier phase to be included in the nanoemulsion containing all emulsifiers and lipid components of the nanoemulsion BF200. According to this procedure BF215 and BF220 was prepared by adapting the amount of the components (see Table 2).

In all examples shown herein, nanoemulsion BF200 was used.

Step 3: Manufacturing of the Nanoemulsion by Mixing the Aqueous Component from Step 1 and the Carrier from Step 2 for a Lipid Content of 10% (BF200)

Manufacturing of an emulsion by mixing 900 g phosphate buffer (from Step 1) and 100 g carrier (from Step 2). First, the aqueous component comprising the phosphate buffer was heated to approximately 45-60° C. in a suitable vessel. Then, the carrier (concentrate) of step 2 was heated to approximately 45-60° C. Subsequently, the carrier was poured to the phosphate buffer under continuous stirring with a propeller mixer resulting in the formation of a stable trombe (or spout) having the maximal possible diameter without causing foaming or sputtering. The resulting nanoemulsion is stirred for 15 min. Finally, the nanoemulsion was cooled down to room temperature.

In nanoemulsion BF215, 850 g phosphate buffer (from Step 1) and 150 g carrier were mixed. In nanoemulsion BF220, 800 g phosphate buffer (from Step 1) and 200 g carrier were mixed.

Step 4: Preparation of the Final Formulation and Primary Packaging

Optionally, the nanoemulsion can be sterilized by filtration.

Depending on the purpose of the nanoemulsion, one may add adjuvants and/or excipients and/or active ingredients (at the appropriate step according to the description) and/or dilute the nanoemulsion with in a way to get a suitable pharmaceutical formulation, e.g., by adding water, a suitable buffer, or an additional aqueous gel base with e.g. poloxamer 407 or xanthan gum.

The pharmaceutical formulations with different nanoemulsions BF200, BF215 and BF220 were filled into a conventional glass container or into a squeeze tube with an appropriate size, respectively.

Example 2: Preparation of Gel Formulation 1, Containing Propylene Glycol (Comparative Example Step 1: Preparation of Nanoemulsion Nanoemulsion BF200 is produced according to Example 1. Sodium benzoate, 5-ALA and propylene glycol were added under stirring to nanoemulsion BF200.

TABLE 4

Composition of Nanoemulsion, based upon BF200

| Component | | Nanoemulsion per 287.35 mg of emulsion |
|---|---|---|
| BF200 | | |
| Soybean Phosphatidylcholine | 3.00 mg | |
| Polysorbate 80 | 6.00 mg | |
| Triglycerides, medium chain (Miglyol 812) | 6.00 mg | |
| Isopropyl alcohol | 2.50 mg | |
| Disodium phosphate dihydrate | 0.03 mg | |
| Sodium dihydrogen phosphate dihydrate | 0.22 mg | |
| Purified water | 157.25 mg | 175.00 mg |
| Components added to BF200 | | |
| 5-aminolevulinic acid hydrochloride | 100.000 mg | |
| Propylene glycol | 10.000 mg | |
| Sodium benzoate | 2.35 mg | 112.350 mg |
| | | 287.35 mg |

Step 2: Preparation of Gel Base with Xanthan Gum (XT).

A round bottom flask was disinfected with isopropanol. Water was put into the bowl and then Xanthan was spread thereon. The resulting basis gel was filled in an appropriate beaker.

TABLE 5

Composition of Gel base

| Component | Gel base per 712.65 mg of gel base | |
|---|---|---|
| Xanthan gum | 28.50 mg | 4.0% |
| Purified water | 684.15 mg | 96.0% |

Step 3: Preparation of Formulation 1.

28.74% of the nanoemulsion produced in step 1 (including 17.5% of nanoemulsion BF200), and 71.26% of Xanthan gel base produced in step 2 are mixed and homogenized, resulting in Formulation 1.

TABLE 6

Components of gel Formulation 1 (nanoemulsion BF200, gel base, 5-ALA, propylene glycol), mg per g gel

| Component | Formulation 1 per 1 g of gel |
|---|---|
| 5-aminolevulinic acid hydrochloride | 100.000 mg |
| Xanthan gum | 28.50 mg |
| Soybean Phosphatidylcholine | 3.00 mg |
| Polysorbate 80 | 6.00 mg |
| Triglycerides, medium chain (Miglyol 812) | 6.00 mg |
| Isopropyl alcohol | 2.50 mg |
| Disodium phosphate dihydrate | 0.03 mg |
| Sodium dihydrogen phosphate dihydrate | 0.22 mg |
| Propylene glycol | 10.000 mg |
| Sodium benzoate | 2.350 mg |
| Purified water | 841.4 mg |

Formulation 1 was filled in a 2 g squeeze tube.

Example 3: Preparation of Gel Formulation 2, Free of Propylene Glycol

Step 1: Preparation of Nanoemulsion

Nanoemulsion BF200 is produced according to Example 1. Sodium benzoate and 5-ALA were added under stirring to nanoemulsion BF200. Formulation 2 is free of propylene glycol. In view of Formulation 1, the propylene glycol was replaced by the corresponding amount of xanthan gel base (10 mg/g, 1%).

TABLE 7

Composition of Nanoemulsion based upon BF200

| Component | | Nanoemulsion per 277.35 mg of emulsion |
|---|---|---|
| BF200 | | |
| Soybean Phosphatidylcholine | 3.00 mg | |
| Polysorbate 80 | 6.00 mg | |
| Triglycerides, medium chain (Miglyol 812) | 6.00 mg | |
| Isopropyl alcohol | 2.50 mg | |
| Disodium phosphate dihydrate | 0.03 mg | |
| Sodium dihydrogen phosphate dihydrate | 0.22 mg | |
| Purified water | 157.25 mg | 175.00 mg |
| Components added to BF200 | | |
| 5-aminolevulinic acid hydrochloride | 100.000 mg | |
| Propylene glycol | 0.000 mg | |
| Sodium benzoate | 2.350 mg | 102.350 mg |
| | | 277.35 mg |

Step 2: Preparation of Gel Base with Xanthan Gum (XT).

The gel based in produced as described in Step 2 of Example 1.

TABLE 8

Composition of Gel base

| Component | Gel base per 722.65 mg of gel base | |
|---|---|---|
| Xanthan gum | 28.90 mg | 4.0% |
| Purified water | 693.75 mg | 96.0% |

Step 3: Preparation of Formulation 2.

27.74% of the nanoemulsion produced in step 1 (including 17.5% of nanoemulsion BF200), and 72.26% of Xanthan gel base produced in step 2 are mixed and homogenized, resulting in Formulation 2.

TABLE 9

Components of gel Formulation 2 (nanoemulsion BF200, gel base, 5-ALA), mg per g gel

| Component | Formulation 2 per 1 g of gel |
|---|---|
| 5-aminolevulinic acid hydrochloride | 100.000 mg |
| Xanthan gum | 28.90 mg |
| Soybean Phosphatidylcholine | 3.0 mg |
| Polysorbate 80 | 6.00 mg |
| Triglycerides, medium chain (Miglyol 812) | 6.00 mg |
| Isopropyl alcohol | 2.5 mg |
| Disodium phosphate dihydrate | 0.03 mg |
| Sodium dihydrogen phosphate dihydrate | 0.22 mg |
| Propylene glycol | 0.000 mg |
| Sodium benzoate | 2.350 mg |
| Purified water | 851.000 mg |

Formulation 2 was filled in a 2 g squeeze tube.

Example 4: Determination of Vesicle Size and Polydispersity Index by Dynamic Light Scattering The size of the nanovesicles, expressed as the z-average size (e.g., in nm), and the homogeneity of nanovesicle formulations, expressed as polydispersity index was determined by dynamic light scattering (sometimes referred as Photon Correlation Spectroscopy (PCS) or Quasi-Elastic Light Scattering (QELS)). The technique is well known in the art and well established to determine size of nano or micro particles or vesicles in emulsions, suspensions or polymeric solutions with a laser. Measurements were conducted with an Zetasizer Nano ZS (Malvern Instruments Ltd, Malvern, Worcestershire, UK). The measurement was performed according to the manufacturer's instructions.

The Zetasizer Nano ZS is instrumented with a 633 nm green laser and optics with a 173° scattering detector angle for size measurement. The device may be operated under vacuum for measurements, but in these cases, vacuum was not applied to the samples for size and homogeneity measurements.

Example 5: Determination of Impurity

Qualitative and quantitative analysis of impurities was performed by LC-MS using positive electrospray ionisation (ESI+). The scan change covered degradation products in a range of 100-2000 m/z.

Example 6: Determination of Viscosity

Viscosity was measured by rotation (measuring geometry: cone/plate) with a constant shear rate of 90.0 $s^{-1}$ at 20° C.

Example A

Content of Impurities in an 5-ALA Nanoemulsion Gel (Compared with a Comparative Formation Containing Propylene Glycol) after Storage for 6 Months Formulation 1 (containing 1% propylene glycol) was prepared as described in Example 2. Formulation 1 (free of propylene glycol) was prepared as described in Example 3.

10-ml glass vials, containing either Formulation 1 or Formulation 2 were stored for six months at 25° C. or 40° C.

Impurities were detected with mass spectroscopy, as described in Example 5.

The results are summarized in FIG. 1. As expected, the ester of 5-ALA and propylene glycol (2-Hydroxypropyl-δ-aminolevulinate) is not present in Formulation 2 (without propylene glycol). An impurity with m/z=246 was found to be present in the comparative Formulation 1 (with propylene glycol) in a mean amount of about 0.3% after storage at 25° C. and 1.2% after storage at 40° C. Unexpectedly, the impurity was found to be present in Formulation 2 (without of propylene glycol) in a mean amount of about 0.15% after storage at 25° C. and 0.6% after storage at 40° C.

This behavior is also illustrated in FIG. 2. Chromatograms of known impurity (2-hydroxypropyl-δ-aminolevulinate; m/z 190) and impurity m/z 246 in Formulation 1 (with propylene glycol) and Formulation 2 (without propylene glycol) after storage for 3 months at 40° C.

Conclusion: A 5-ALA formulation, being free of propylene glycol, is safer/pharmaceutically more tolerable than a comparative 5-ALA formulation, containing propylene glycol.

Example B

Ex-Vivo Skin Penetration Study with Human Eye Lid Skin

Formulation 1 (with propylene glycol) was prepared as described in Example 2. Formulation 2 (without of propylene glycol) was prepared as described in Example 3.

Objective
    Comparison of skin penetration properties of Formulation 1 (with propylene glycol) and Formulation 2 (without propylene glycol)
    Assess the amount of protoporphyrin IX (PpIX) in skin biopsy samples in fresh, vital skin samples after drug application.

Experimental Set-Up
Test Material
    Human upper eyelid skin from routine blepharoplastic surgeries (eyelid tightening)
    Formulation 1 with propylene glycol (batch no. 166M, (1) in FIG. 3)
    Formulation 2 without propylene glycol (batch no. 111M, (2) in FIG. 3)

Methodology
  Incubation of skin explants with formulation for 0, 1, 3 h
  Cryosectioning, extraction of protoporphyrin IX from skin sections
  PpIX extraction from tissues and fluorimetric analysis of PpIX content in lysates
Results
  The results are summarized in FIG. 3.
  Means of n=5 plotted against (incubation) time.
  PpIX concentrations increase with incubation time.
  Although propylene glycol is a well-known penetration enhancer, equivalent penetration results were achieved with new Formulation 2 without propylene glycol compared to comparative Formulation 1 with propylene glycol (the formulation without propylene glycol is non-inferior to formulation with propylene glycol).
  Differences between formulations at different time points were not statistically significant (Mann-Whitney's U-test)
  Conclusion: A 5-ALA formulation, being free of propylene glycol, which is found to be more stable that a comparative 5-ALA formulation, containing propylene glycol (Example 1), provides equivalent penetration efficacy.

Example C

In Vitro Release Test of 5-Aminolevulinic Acid from Formulation 1 (with Propylene Glycol) and Formulation 2 (without Propylene Glycol)
  Formulation 1 (with propylene glycol) was prepared as described in Example 2 (Batch 166M).
  Formulation 2 (without propylene glycol) was prepared as described in Example 3 (Batch 110M).
Objective
  Method development and evaluation of in vitro release (acc. to SUPAC-SS guideline (FDA, SUPAC, 1997)) of ALA from gel formulations (GMP GLP)
Experimental Set-Up
Test Material
  Synthetic membranes (nylon, 0.20 μm)
  IVRT (in vitro release test) with so-called "Franz diffusion cell", FIG. 4
  Formulation 1 with propylene glycol (comparative gel)
  Formulation 2 without propylene glycol
Methodology.
  Analytical method for quantification of ALA: HPLC-MS/MS
Drug Application, Sampling and Analysis
  Application of 300 mg ALA nanoemulsion to nylon membrane (0.20 μm)
  Incubation at 32+−1° C. and sampling at t=20, 40, 60, 90, 120, and 150 min
  n=6 for each formulation (with/without propylene glycol) →12 Franz cells
  HPLC-MS/MS for quantification of ALA in receptor compartment
Results
  The results are described in FIG. 5:
  Higuchi plot (Takeru Higuchi 1961: "Rate of release of medicaments from ointment bases containing drugs in suspension" (DOI: 10.1002/jps.2600501018), cumulative transport of 5-ALA (in μg cm$^{-2}$), against square root of time (in h$^{-0.5}$).
  Transported amount is higher for Formulation 2 without propylene glycol
  The standard deviations two curves overlap completely.
  There is no significant difference between the two tested formulations
  Statistical comparison of the slopes of the release curve:

TABLE 10

| Formulation 1 | Formulation 2 | Limits of the 90% confidence interval | | |
|---|---|---|---|---|
| with propylene glycol | without propylene glycol | Lower Limit 8$^{th}$ value (0.75) | Upper-limit 29$^{th}$ value (1.33) | Significant difference |
| Batch 166M K27033 Test Item A | Batch 110M K27080 Test Item B | 0.816 | 1.036 | No |

There is no significant difference between the two tested formulations.
  The formulation without propylene glycol is to be considered at least as good as the formulation with propylene glycol in terms of drug release.
  Conclusion: A 5-ALA gel formulation, being free of propylene glycol, which is found to be more stable that a comparative 5-ALA formulation, containing propylene glycol (Example 1), provides an equivalent in vitro release profile.

The invention claimed is:

1. A formulation comprising:
   (a) a nanoemulsion comprising:
      (i) at least one aqueous component;
      (ii) a carrier component comprising:
         (1) at least one lipophilic component,
         (2) at least one surfactant, and
         (3) at least one alcohol; and
   (b) 5-aminolevulinic acid and/or a derivative, a precursor, a metabolite, and/or a pharmaceutically acceptable salt thereof,
   wherein the formulation comprises essentially no propylene glycol and essentially no sorbitol.

2. The formulation of claim 1, wherein the formulation further comprises less than 1% w/w of a non-cyclic polyol having 2 to 5 carbon atoms.

3. The formulation of claim 1, wherein the formulation further comprises less than 1% w/w of a non-cyclic polyol having 2 to 12 carbon atoms.

4. The formulation of claim 1, wherein the at least one alcohol comprises: 3, 4, or 5 carbon atoms; or 1-propanol, 2-propanol, or a mixture thereof.

5. The formulation of claim 1, comprising the at least one aqueous component in an amount from 50% to 99% (w/w), from 70% to 95% (w/w), from 75% to 95% (w/w), or from 80% to 90% (w/w).

6. The formulation of claim 4, comprising the at least one lipophilic component in an amount from 0.1% to 30% (w/w), from 0.25% to 15% (w/w), from 0.25% to 10% (w/w), from 2% to 10% (w/w), or 3% to 8% (w/w) based on total weight of the nanoemulsion.

7. The formulation of claim 1, wherein the formulation comprises no propylene glycol.

8. The formulation of claim 1, wherein the formulation further comprises less than or equal to 0.99%, 0.95%, 0.9%, 0.8%, 0.7%, 0.6%, 0.5%, 0.4%, 0.3%, 0.2%, or 0.1% w/w of a non-cyclic polyol having 2 to 5 carbon atoms.

9. The formulation of claim 1, wherein the formulation further comprises essentially no non-cyclic polyol having 2 to 5 carbon atoms.

10. The formulation of claim 1, wherein the formulation further comprises no non-cyclic polyol having 2 to 5 carbon atoms.

11. The formulation of claim 1, wherein the formulation further comprises less than or equal to 0.99%, 0.95%, 0.9%, 0.8%, 0.7%, 0.6%, 0.5%, 0.4%, 0.3%, 0.2%, or 0.1% w/w of a non-cyclic polyol having 2 to 12 carbon atoms.

12. The formulation of claim 1, wherein the formulation further comprises essentially no non-cyclic polyol having 2 to 12 carbon atoms.

13. The formulation of claim 1, wherein the formulation further comprises no non-cyclic polyol having 2 to 12 carbon atoms.

14. The formulation of claim 1, wherein the at least one lipophilic component comprises: triglycerides and/or mixtures thereof; or a caprylic triglyceride, a capric triglyceride, or a mixture thereof.

15. The formulation of claim 1, wherein the at least one surfactant comprises: a phospholipid, a phosphatidylcholine, a lysophospholipid, a ceramide, and/or a mixture thereof; and/or a polyoxyethylene-type surfactant.

16. The formulation of claim 4, wherein the at least one alcohol is in an amount from 0.1% to 10% (w/w), from 0.5% to 5% (w/w), from 1% to 5% (w/w), or from 1% to 3% based on total weight of the nanoemulsion.

17. The formulation of claim 1, wherein the formulation further comprises essentially no monosaccharides and disaccharides.

* * * * *